United States Patent
Ramos Macias et al.

(10) Patent No.: US 12,186,560 B2
(45) Date of Patent: Jan. 7, 2025

(54) VESTIBULAR STIMULATION PROSTHESIS

(71) Applicants:Cochlear Limited, Macquarie University (AU); University of Las Palmas de Gran Canaria, Las Palmas de Gran Canaria (ES)

(72) Inventors: Angel Manuel Ramos Macias, Las Palmas de Gran Canaria (ES); Angel Ramos De Miguel, Las Palmas de Gran Canaria (ES); Koen Erik Van Den Heuvel, Macquarie University (AU); Mattheus Johannes Petrus Killian, Macquarie University (AU)

(73) Assignees: Cochlear Limited, Macquarie University (AU); University of Las Palmas de Gran Canaria, Las Palmas de Gran Canaria (ES)

( * ) Notice: Subject to any disclaimer, the term of this patent is extended or adjusted under 35 U.S.C. 154(b) by 0 days.

(21) Appl. No.: 18/507,403

(22) Filed: Nov. 13, 2023

(65) Prior Publication Data
US 2024/0082577 A1    Mar. 14, 2024

Related U.S. Application Data

(63) Continuation of application No. 16/816,965, filed on Mar. 12, 2020, now abandoned.

(30) Foreign Application Priority Data

Jul. 24, 2019  (EP) .................................... 19382629

(51) Int. Cl.
*A61N 1/05*    (2006.01)
*A61N 1/36*    (2006.01)
*A61N 1/372*   (2006.01)

(52) U.S. Cl.
CPC ......... *A61N 1/3606* (2013.01); *A61N 1/0541* (2013.01); *A61N 1/36142* (2013.01); *A61N 1/372* (2013.01)

(58) Field of Classification Search
None
See application file for complete search history.

(56) References Cited

U.S. PATENT DOCUMENTS 4,850,962 A * 7/1989 Schaefer .................. A61F 2/18
                                                      607/57
7,225,028 B2   5/2007 Della Santina et al.
(Continued)

FOREIGN PATENT DOCUMENTS

WO    01/60282 A2    8/2001
WO    2013/134873 A1  6/2013
(Continued)

OTHER PUBLICATIONS

European Search Report for European Application No. 20163946.5, dated May 12, 2020, 7 pages.

*Primary Examiner* — Erica S Lee
(74) *Attorney, Agent, or Firm* — Edell, Shapiro & Finnan, LLC

(57) ABSTRACT

A vestibular stimulation prosthesis can restore vestibular function in recipients having vestibular deficiency. In an example, a body is appended onto or within the recipient's ossicular chain such that the body directly interfaces with an oval window of an inner ear of the recipient. Electrical stimulation is provided using one or more electrodes of the body to stimulate the vestibular system and thereby restore vestibular functioning. In an example, a stimulator device connected to the body via a lead is also implanted. The stimulator device can have a small and convenient form factor. In some instances, the stimulator device is a stand-alone device that is configured to provide stimulation to the
(Continued)

recipient's vestibular system without respect to signals received from devices external to the recipient. In some implementations, the stimulator device is a component of a sensory prosthesis (e.g., a cochlear implant or bionic eye) or another medical device.

19 Claims, 19 Drawing Sheets

(56) References Cited

U.S. PATENT DOCUMENTS

| | | | |
|---|---|---|---|
| 8,843,217 B1* | 9/2014 | Keller | A61N 5/0622 607/137 |
| 9,089,692 B2 | 7/2015 | Risi et al. | |
| 2009/0163978 A1 | 6/2009 | Miller et al. | |
| 2009/0240099 A1 | 9/2009 | Conn | |
| 2009/0306457 A1 | 12/2009 | Parker et al. | |
| 2010/0228319 A1 | 9/2010 | Choi et al. | |
| 2010/0324355 A1 | 12/2010 | Spitaels et al. | |
| 2011/0093039 A1 | 4/2011 | Van den Heuvel | |
| 2012/0078337 A1 | 3/2012 | Darley et al. | |
| 2012/0158112 A1 | 6/2012 | Jolly et al. | |
| 2013/0066424 A1 | 1/2013 | Moynahan | |
| 2013/0096654 A1 | 4/2013 | Jaeger et al. | |
| 2013/0184788 A1 | 7/2013 | Jaeger et al. | |
| 2015/0032186 A1* | 1/2015 | Cushing | A61N 1/36038 607/57 |
| 2015/0039057 A1 | 2/2015 | Della Santina et al. | |
| 2015/0066126 A1 | 3/2015 | Marx et al. | |
| 2016/0166828 A1 | 6/2016 | Yu | |
| 2017/0180889 A1* | 6/2017 | Walraevens | H04R 23/02 |
| 2018/0021568 A1 | 1/2018 | Schachtele et al. | |
| 2018/0304077 A1* | 10/2018 | Lee | A61N 1/37229 |
| 2019/0167977 A1* | 6/2019 | Risi | A61N 1/0551 |
| 2019/0167985 A1 | 6/2019 | Carlson | |
| 2019/0274596 A1 | 9/2019 | Boven et al. | |
| 2020/0330775 A1 | 10/2020 | Unterweissacher et al. | |
| 2021/0131251 A1 | 5/2021 | Bhatnagar | |

FOREIGN PATENT DOCUMENTS

| | | |
|---|---|---|
| WO | 2014/165462 A1 | 10/2014 |
| WO | 2015/077773 A1 | 5/2015 |
| WO | 2017/081335 A1 | 5/2017 |

* cited by examiner

VESTIBULAR STIMULATION PROSTHESIS

RELATED APPLICATION

This application is a continuation of U.S. application Ser. No. 16/816,965, filed Mar. 12, 2020, which claims the benefit of European Patent Application No. 19382629.4, filed Jul. 24, 2019, and which is hereby incorporated herein by reference in its entirety. To the extent appropriate, a claim of priority is made to the above disclosed application.

STATEMENT OF FUNDING

The project leading to this application has received funding from the European Union's Horizon 2020 research and innovation programme under grant agreement No 801127.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In an example, there is an apparatus comprising: a flexible body having one or more electrodes; an implantable housing remote from the flexible body; a stimulator disposed in the implantable housing and configured to deliver stimulation to vestibular tissue of a recipient through an oval window of the recipient via the one or more electrodes; and a lead for electrically connecting the one or more electrodes to the stimulator.

In another example, there is a method comprising: surgically accessing an implantation area in a recipient; placing one or more electrodes of a flexible body of a vestibular stimulation prosthesis proximate an oval window of the recipient; implanting the flexible body at least partially in contact with an ossicular chain of the recipient; and finishing implantation.

In another example, a method comprising: via a flexible body disposed in a recipient: conducting vibrations from an ossicular chain to an inner ear of the recipient; and electrically stimulating vestibular tissue of the recipient.

In another example, an ossicular chain prosthesis comprising: one or more electrodes; a body configured to be disposed proximate an oval window of a recipient to deliver stimulation to vestibular tissue of a recipient through the oval window via the one or more electrodes; and a coupling configured to couple the body with a bone of the recipient's auditory ossicles.

In another example, there is an apparatus comprising: a reference electrode; a lead coupled to the reference electrode for electrically coupling the reference electrode to another component; and a reference electrode fastener configured to fasten the reference electrode to middle ear anatomy.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
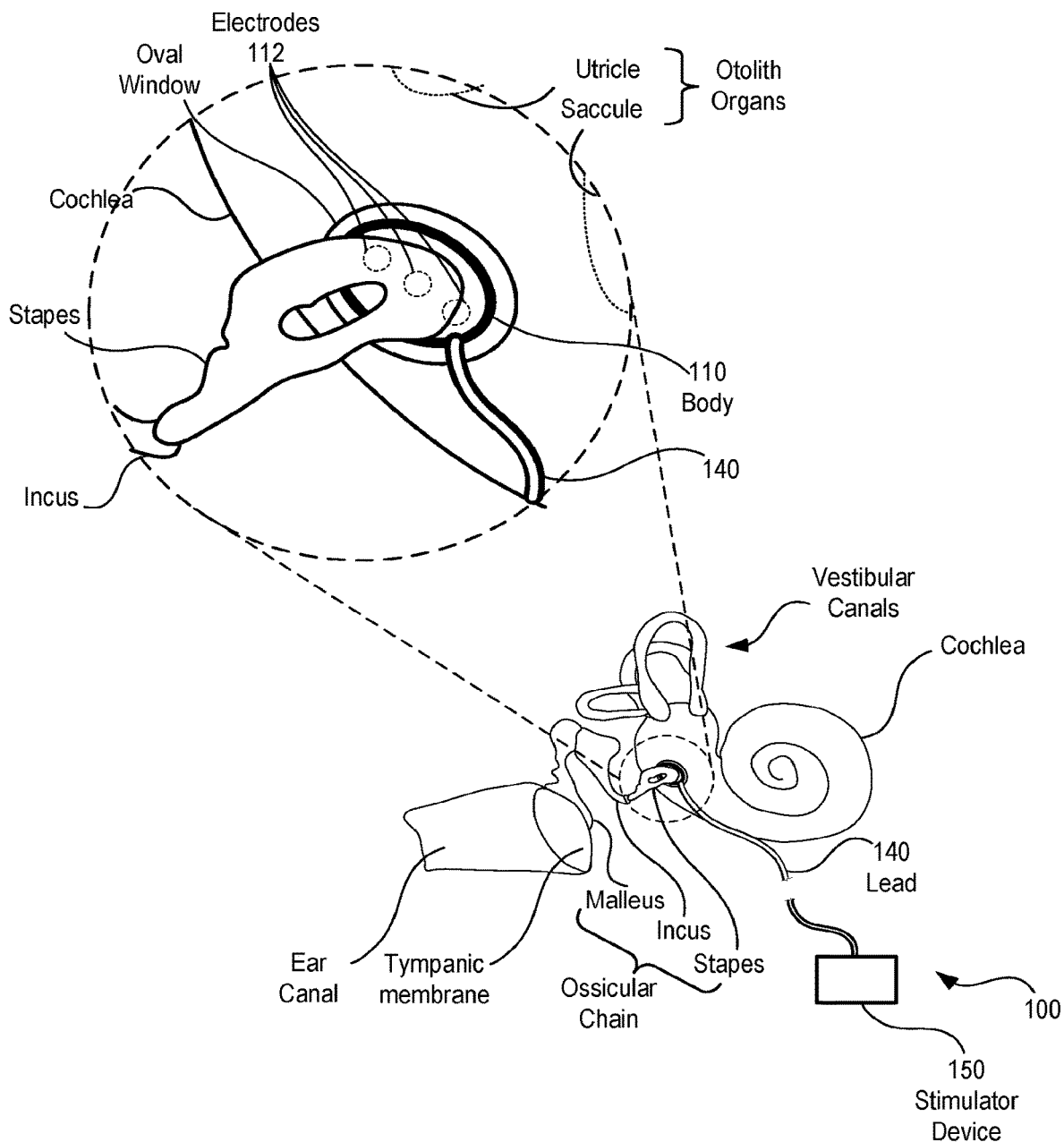
FIG. 1 illustrates an example view of a vestibular stimulation prosthesis implanted relative to inner ear anatomy in accordance with certain embodiments herein.

Sensory impulses relating to balance and spatial orientation are generated by the human vestibular system. These sensory impulses are perceived by the brain via the vestibulocochlear nerve and provide a sense of balance and spatial orientation. But disorders affecting the vestibular system (e.g., Ménière's disease, other bilateral vestibular disorders, or inflammation of vestibular anatomy) can cause vestibular deficiency by interfering with these sensory impulses, thereby negatively affect one's sense of balance and spatial orientation. Vertigo can also result.

Disclosed embodiments include vestibular stimulation prostheses for restoring vestibular function in recipients having vestibular deficiency. In an example, a body (e.g., a flexible a mesh-like body) is appended onto or within the recipient's ossicular chain such that the body directly interfaces with an oval window of an inner ear of the recipient. Electrical stimulation is provided using one or more electrodes of the body to stimulate the vestibular system (e.g., the otolith organs thereof) and thereby restore vestibular functioning. In an example, a stimulator device connected to the body via a lead is also implanted. The stimulator device can have a small and convenient form factor. In some instances, the stimulator device is a stand-alone device that is configured to provide stimulation to the recipient's vestibular system without respect to signals received from devices external to the recipient. In some implementations, the stimulator device can be a component of a sensory prosthesis (e.g., a cochlear implant or bionic eye) or another medical device.

The body of the vestibular stimulation prosthesis can interface directly with a recipient's oval window. In one example, the body is configured to be placed between the stapes and the oval window. In another example, the body also acts as a stapes prosthesis. For instance, the body can connect to the incus. In addition, the body can be configured to preserve inner ear anatomy. For instance, the body and the components thereof (e.g., the electrodes thereof) can be configured to avoid penetrating into the inner ear. This placement of the body within the ossicular chain can result in approximately 10 Decibels or less of hearing loss for the recipient due to attenuation of vibrations conducted to the oval window. However the hearing loss can be preferable in many instances compared to the potentially worse outcomes that can result from alternative approaches penetrating the inner ear (e.g., damaging hearing or vestibular anatomy).

Positioning the body proximate to the oval window can provide several advantages. First, the oval window is sufficiently close to the otolith organs to provide relatively easy targeting of stimulation to the otolith organs. Additionally, the stimulation signals from the electrodes can more easily penetrate through the oval window than other bony structure within the middle ear cavity (e.g., the temporal bone). This can allow for the use of relatively lower intensity stimulation and relatively lower collateral damage to tissue. Further, the placement proximate the oval window can be performed transtympanically, which is less invasive than traditional approaches through the temporal bone.

Figure 38:
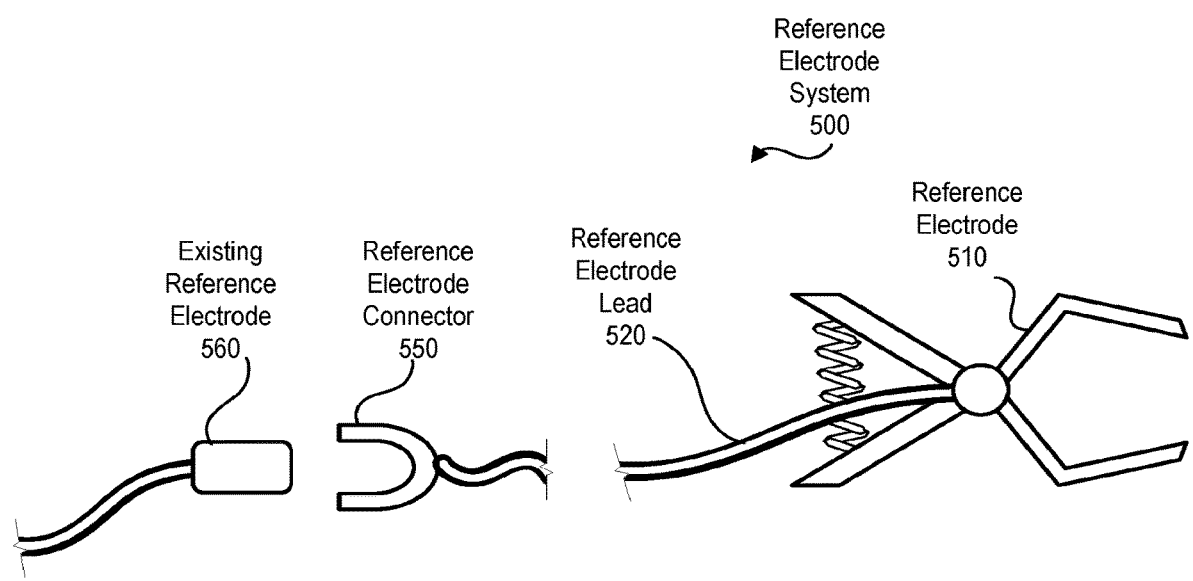
FIG. 38 illustrates an example configuration of the reference electrode system in which the reference electrode system can extend an existing reference electrode in accordance with certain embodiments herein.
Figure 39:
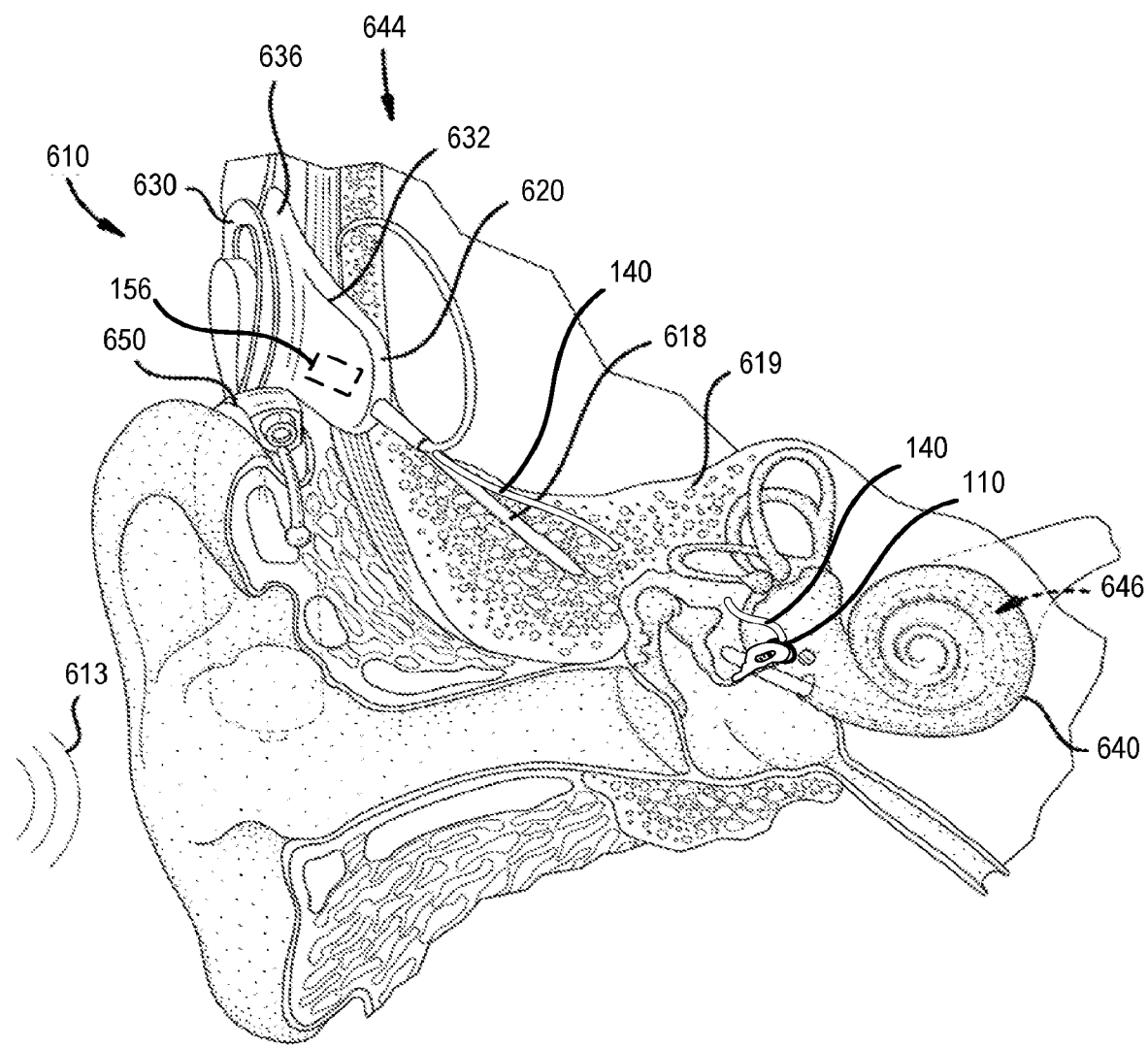
FIG. 39 illustrates an example cochlear implant system that can benefit from use of the technologies disclosed herein.

Disclosed embodiments further include particular electrode and body arrangements and designs for use with vestibular stimulation prostheses (see, e.g., FIGS. 3-20), particular coupling arrangements and designs for connecting the body with anatomy of the recipient (see, e.g., FIGS. 21-26), processes for implanting the vestibular stimulation prosthesis and providing therapeutic stimulation (see, e.g., FIGS. 27 and 28), example reference electrode configurations (see, e.g., FIGS. 29-38), and an example implementation of the vestibular stimulation prosthesis with a sensory prosthesis (see, e.g., FIG. 39).

As should be appreciated, while particular examples are illustrated and discussed herein, the disclosed vestibular stimulation prostheses and processes described herein can be integrated in any of a variety of ways in accordance with many embodiments of the invention. The discussion is not meant to suggest that the disclosed vestibular stimulation examples are only suitable for implementation within systems akin to that illustrated in and described herein. In general, additional configurations can be used to practice the methods and systems herein and/or some aspects described can be excluded without departing from the processes and systems disclosed herein.

Vestibular Stimulation Prosthesis

FIG. 1 illustrates a view of an example vestibular stimulation prosthesis 100 implanted relative to inner ear anatomy in accordance with certain embodiments herein. The vestibular stimulation prosthesis 100 is an apparatus configured to provide therapeutic stimulation to a vestibular system of a recipient. In the illustrated configuration, the vestibular stimulation prosthesis 100 includes a body 110 having one or more electrodes 112. The body 110 is connected to a stimulator device 150 via a lead 140. Other configurations of the vestibular stimulation prosthesis 100 are also possible.

The body 110 can be a carrier for one or more components of the vestibular stimulation prosthesis 100. In particular, the body 110 be a carrier for one or more components for providing stimulation to the vestibular system, such as the one or more electrodes 112. The body 110 can be configured to be placed proximate the oval window. The body 110 can include other components, such as one or more components for connecting the body 110 to the ossicular chain (e.g., the stapes, incus, or malleus thereof). Such connectors are described in more detail in relation to FIGS. 20-25. The body 110 can further include one or more sensors (e.g., for sensing the vestibular system).

The body 110 can take any of a variety of forms. In an example, the body 110 is formed as a mesh. In an example, the mesh is relatively flexible. In an example, the body is formed with an elastomer, such as silicone. In an example, the body 110 is configured to conduct vibrations from the ossicular chain to the oval window. The body 110 can be configured to interface with the oval window. The body 110 can be configured to cover part of or the entirety of the oval window. The body 110 can be configured to cover the oval window in such a manner that one or more electrodes 112 are positioned to target vestibular anatomy of the recipient.

The one or more electrodes 112 are electrically-conductive components via which stimulation can be provided. The one or more electrodes 112 can have any of a variety of different shapes, sizes, profiles, and configurations. Example configurations of the electrodes 112 are shown in FIGS. 3-17. Generally, the one or more electrodes 112 can be advantageously configured to resist penetrating the oval window when the body 110 is properly implanted. IN other examples, the one or more electrodes 112 can be configured to penetrating the oval window to a predetermined depth, avoiding anatomical damage of otolith organ.

The lead 140 is a component that electrically connects two or more components of the vestibular stimulation prosthesis 100. In many examples, the lead 140 is a cable having one or more wires disposed within an insulated sheath. In the illustrated configuration, the lead 140 connects the stimulator device 150 to the body 110. In such a configuration, the lead 140 can convey electrical stimulation signals from the stimulator device 150 to the body 110 (e.g., to the electrodes 112 thereof).

Figure 2:
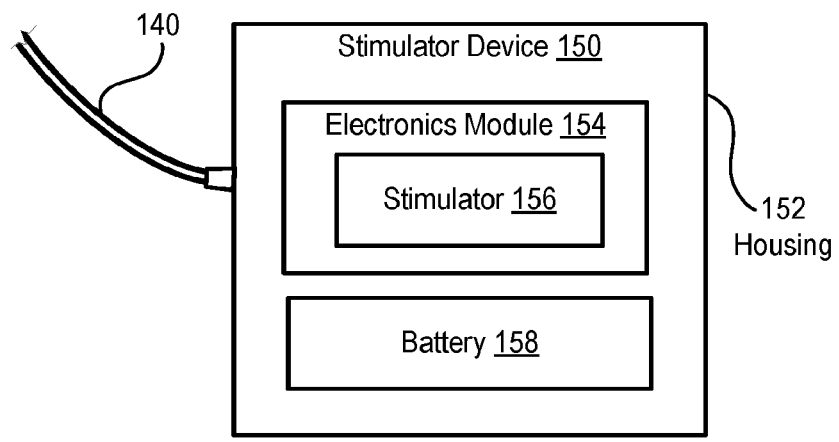
FIG. 2 illustrates an example implementation of a stimulator device of the vestibular stimulation prosthesis in accordance with certain embodiments herein.

The stimulator device 150 can be a component of the vestibular stimulation prosthesis 100 that generates the stimulation signals that are to be applied to the vestibular system. The stimulator device 150 often includes a housing in which one or more components are disposed. An example, configuration of the stimulator device 150 is shown in FIG. 2.

The figure further shows the vestibular stimulation prosthesis 100 disposed in relation to vestibular and auditory anatomy. Among the anatomy shown, is the ear canal, which is part of the auditory anatomy. Acoustic pressure or sound waves can be channeled into and through ear canal. Disposed across an end of ear canal is a tympanic membrane which vibrates in response to the sound wave. This vibration is coupled to oval window (also known as the fenestra ovalis), which is adjacent round window (not shown), through the bones of the middle ear. The bones of the middle ear are the malleus, the incus, and the stapes, collectively referred to as the ossicles or the ossicular chain. The ossicles are positioned in the middle ear cavity and serve to filter and amplify the sound wave 103. The ossicles cause the oval window to articulate (e.g., vibrate) in response to the vibration of tympanic membrane. This vibration of the oval window sets up waves of fluid motion of the perilymph within cochlea. Such fluid motion, in turn, activates tiny hair cells (not shown) inside of cochlea. Activation of the hair cells causes appropriate nerve impulses to be generated and transferred through the spiral ganglion cells (not shown) and auditory nerve (not shown) to the brain (also not shown) where they are perceived as sound.

In addition to the auditory anatomy, vestibular anatomy is also shown: the vestibular canals (also known as the semicircular canals) and the otolith organs. The vestibular canals are three canals (known as the horizontal canal, the superior canal, and the posterior canal) that allow rotational movement to be sensed. The otolith organs, which include the utricle and saccule, allow linear movement to be sensed. Rotational and linear movement cause appropriate nerve impulses to be generated via the vestibular anatomy and transferred through the auditory nerve (not shown) to the brain (also not shown) where they are perceived as motion.

The human skull is formed from a number of different bones that support various anatomical features. These bones are omitted from FIG. 1 to aid the viewer. The temporal bone is situated at the side and base of the recipient's skull. The temporal bone is covered by a portion of the recipient's skin, muscle, and fat, which can collectively be referred to as tissue. The temporal bone can be referred to as having a superior portion and a mastoid portion. The superior portion comprises the section of the temporal bone that extends superior to the auricle. That is, the superior portion is the section of the temporal bone that forms the side surface of the skull. The mastoid portion is positioned inferior to the superior portion and is the section of the temporal bone that surrounds the middle ear.

The various components of the vestibular stimulation prosthesis 100 can be disposed with reference to this anatomy. In particular, the illustrated configuration shows the body 110 (and thus the one or more electrodes 112) disposed at least partially between the stapes and the oval window of a recipient's left or right auditory anatomy. In this position, the body 110 is further proximate the otolith organs to which stimulation can be delivered through the oval window. As illustrated, the body 110 covers only a portion of the oval window. In other examples, the body 110 can entirely cover the oval window. In addition, while the stimulator device 150 is illustrated as being located inferior to the cochlea, the stimulator device 150 can be located in any of a variety of locations. The stimulator device 150 is described in more detail in relation to FIG. 2.

Stimulator Device

FIG. 2 illustrates an example implementation of the stimulator device 150. As illustrated, the stimulator device includes an electronics module 154 and a battery 158 disposed within a housing 152.

The housing 152 can be an encasement that surrounds and hermetically seals one or more components of the stimulator device 150. In examples, the housing 152 comprises a biocompatible material. In examples, the housing 152 includes a header providing an interconnection between the lead 140 and one or more components within the stimulator device 150 (e.g., the electronics module 154 thereof).

The electronics module 154 can include one or more other components to provide vestibular stimulation functionality. In some examples, the electronics module 154 includes one or more components for receiving a signal from an external device and converting the signal into a stimulation signal. But in many examples, the electronics module 154 generates a stimulation signal without regard to a signal from an external device. In many examples, the stimulation signal is generated according to a predetermined stimulation schedule that defines when and at what intensity the stimulation is to be applied.

In some examples, the electronics module 154 includes one or more processors (e.g., central processing units) coupled to memory components (e.g., flash memory) storing instructions that when executed cause performance of an operation described herein. In examples, the electronics module 154 generates and monitors parameters associated with generating and delivering the stimulus (e.g., output voltage, output current, or line impedance). In examples, the electronics module 154 generates a telemetry signal that includes telemetry data based on one or more of the parameters. The electronics module 154 can send the telemetry signal to an external device or store the telemetry signal in memory for later use or retrieval.

As illustrated, the electronics module 154 can include a stimulator 156. The stimulator 156 generates electrical stimulation signals for use in stimulating tissue. The stimulator 156 can use stimulation control signals generated by the electronics module 154 (e.g., based on a stimulation schedule) to generate electrical stimulation signals (e.g., current signals) for delivery to the recipient's vestibular anatomy via the one or more electrodes 112. In this way, the vestibular stimulation prosthesis 100 electrically stimulates the recipient's vestibular anatomy (e.g., nerve cells thereof), in a manner that causes the recipient to perceive vestibular percepts. The stimulation can be bipolar stimulation or monopolar stimulation.

The battery 158 is a component configured to store power. The battery 158 includes, for example, one or more rechargeable or non-rechargeable batteries. In some examples, the stimulator device 150 can be configured to receive power from another device, such as an external device or another implanted device. The power stored by the battery 158 can be distributed to the other components of the stimulator device 150 as needed for operation.

The stimulator device 150 can be a standalone vestibular stimulation prosthesis. In other examples, the vestibular stimulation prosthesis 100 can be part of another implanted medical device to add vestibular stimulation capabilities to the device. For instance, the implanted medical device can be a sensory prosthesis relating to one or more of the recipient's senses. For example, the sensory prosthesis can be a prosthesis relating to one or more of the five traditional senses (vision, hearing, touch, taste, and smell) and/or one or more of the additional senses. The sensory prosthesis can be an auditory prosthesis medical device configured to treat a hearing-impairment of the recipient. Where the sensory prosthesis is an auditory prosthesis, the sensory prosthesis can take a variety of forms including a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, a tooth-anchored hearing device, a personal sound amplification product, other auditory prostheses, and combinations of the foregoing (e.g., binaural systems that include a prosthesis for a first ear of a recipient and a prosthesis of a same or different type for the second ear). In examples, the sensory prosthesis can be or include features relating to bionic eyes. Technology disclosed herein can also be relevant to applications with devices and systems used in for example, sleep apnea management, tinnitus management, and seizure therapy. Technology disclosed herein can be used with sensory devices such as consumer auditory devices (e.g., a hearing aid or a personal sound amplification product). Additional details regarding implementation of the vestibular stimulation prosthesis 100 with another implanted medical device is described in relation to FIG. 39.

The stimulator device 150 can be connected via the lead 140 to the body 110 for providing stimulation via the electrodes 112. The body 110 and the electrodes can take any of a variety of different configurations, including those described in relation to FIGS. 3-20.

In some examples, the stimulator device 150 (and the vestibular stimulation prosthesis 100 as a whole) can include one or more aspects of the devices, methods, and computer programs for generating one or more signals for the electrical stimulation of the saccule and utricle of a patient as described in WO 2017/081335, which is hereby incorporated by reference in its entirety for any and all purposes.

Body and Electrodes

Figure 3:
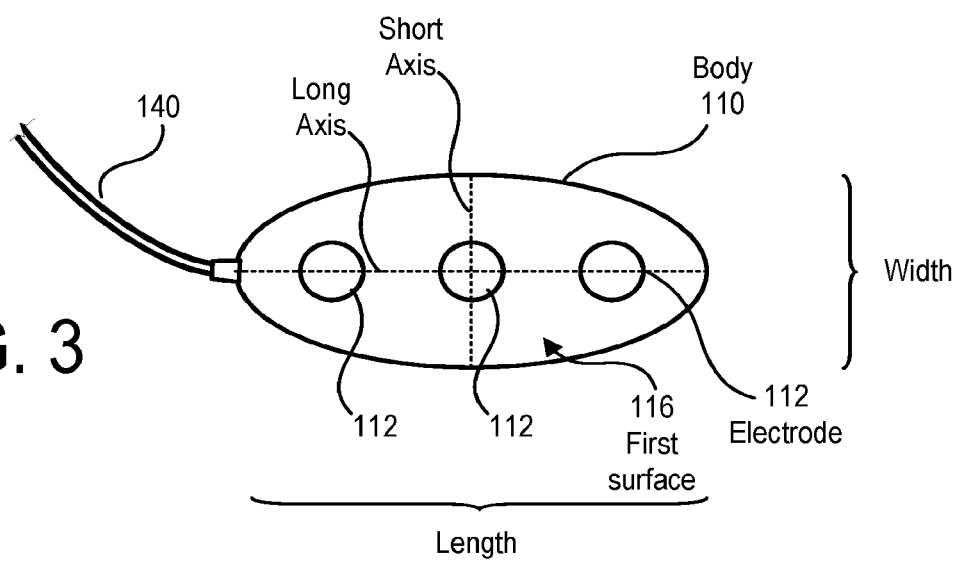
FIG. 3 illustrates an example front view of a body of a vestibular stimulation prosthesis in accordance with certain embodiments herein.
Figure 4:
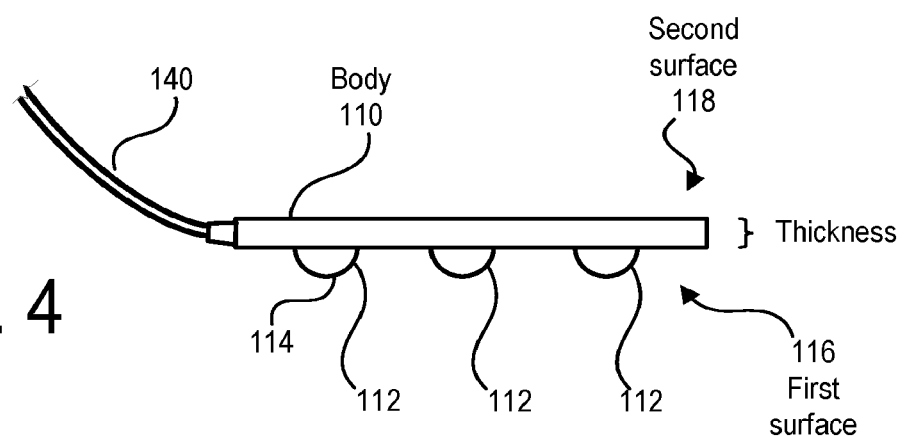
FIG. 4 illustrates a side view of the body of FIG. 3 in accordance with certain embodiments herein.

FIG. 3 illustrates a front view of an example body 110, and FIG. 4 illustrates a side view of the example body 110 of FIG. 3. In the illustrated configuration, the body 110 has an oval shape with a long axis being longer than a short axis. The thickness of the body 110 is less than the width of the body 110, which is less than the length of the body 110. The body 110 includes three electrodes 112 disposed linearly along the long axis. The three electrodes 112 protrude from the body 110 and have a dome shape. The electrodes 112 each have respective tips 114, which are rounded. The roundness of the respective tips 114 contributes to the electrodes 112 resisting penetration into the oval window when the body 110 is implanted proximate the oval window. The lead 140 extends laterally from the body 110. The illustrated configuration is just one example implementation and others are also possible.

As illustrated, the body 110 can define a first surface 116 and a second surface 118. The first surface 116 can be a surface (e.g., a side or face of the body 110) configured to be disposed proximate (e.g., configured to contact) oval window tissue of a recipient when the body 110 is implanted in the recipient. In many examples, the first surface 116 is the surface of the body 110 at which the electrodes 112 are disposed. The second surface 118 can be a surface of the body 110 configured to be disposed proximate (e.g., configured to contact) an ossicular chain of the recipient. In examples, the second surface 118 is a surface at which a coupling for connecting the body 110 to the ossicular chain is disposed (see, e.g., coupling 400 shown in FIGS. 21-26).

The body 110 can take any of a number of different shapes. In examples, the body 110 can have the shape of an n-sided polygon, where n is an integer three or greater (e.g., a triangle, quadrilateral, pentagon, etc.), when viewed from the front of the body 110. In examples, the body 110 can have the shape of an n-pointed star polygon, where n is an integer five or greater (e.g., a pentagram, a hexagram, heptagram, etc.), when viewed from the front of the body 110. The corners of the body 110 can be rounded or sharp. In the elevation view of FIG. 4, the body 110 is flat. In other examples, the body 110 can have concavities, convexities, ridges, waves, or other structural features. In an example, a flexible body 110 is a body sufficiently flexible to conform to a shape of a recipient's oval window when implanted. The body 110 can be constructed using any of a variety of materials, such as elastomers (e.g., silicone).

Generally, the configurations of the body 110 can be selected to properly position the electrodes 112 to target vestibular anatomy to deliver therapeutic stimulation. For example, the body 110 can be sized and shaped to facilitate placement of the electrodes 112 proximate target tissue. The body 110 can be sized and shaped to facilitate useful contact between the body 110 and the oval window. In addition or instead, the configurations of the body 110 can be selected to facilitate the conduction of vibrations from the ossicular chain to the oval window. For instance, the body can be sized and shaped to do so. Further, the materials of the body 110 can be selected to have sufficient stiffness or other properties to be conducive to the transmission of vibrations to the oval window. Further, the body 110 can be configured to preserve inner ear anatomy of the recipient. For example, the body 110 can be configured to resist damaging inner ear anatomy (e.g., by having rounded or blunt shapes or protrusions). Example configurations of the body 110 (and its components) are shown in FIGS. 5-11.

Body Configurations

Figure 5:
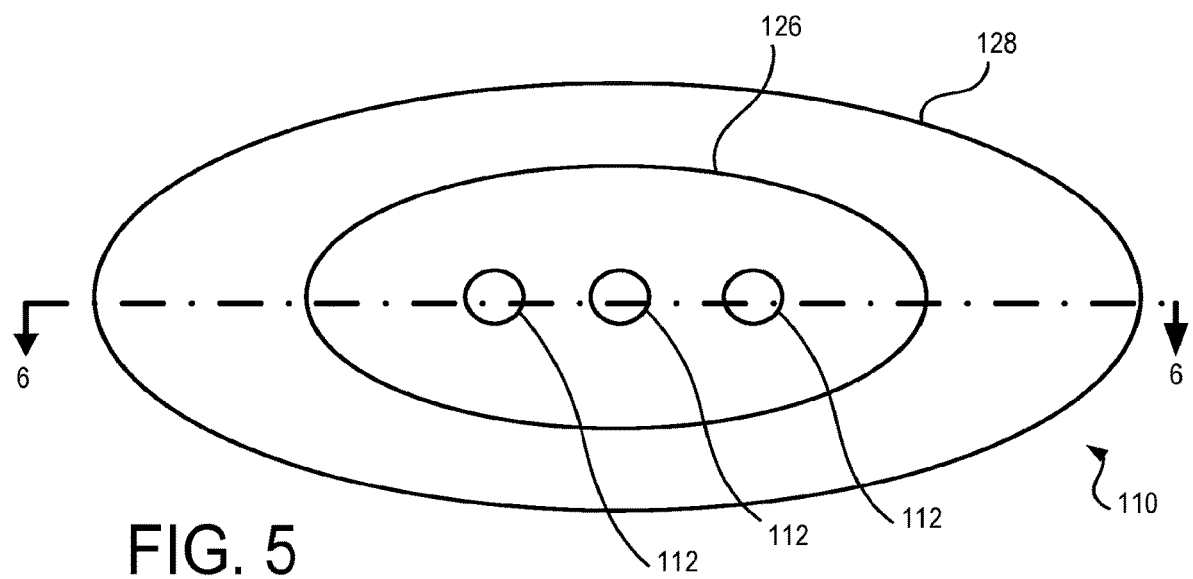
FIG. 5 illustrates an example front view of the body having an inner portion and an outer portion in accordance with certain embodiments herein.
Figure 6:
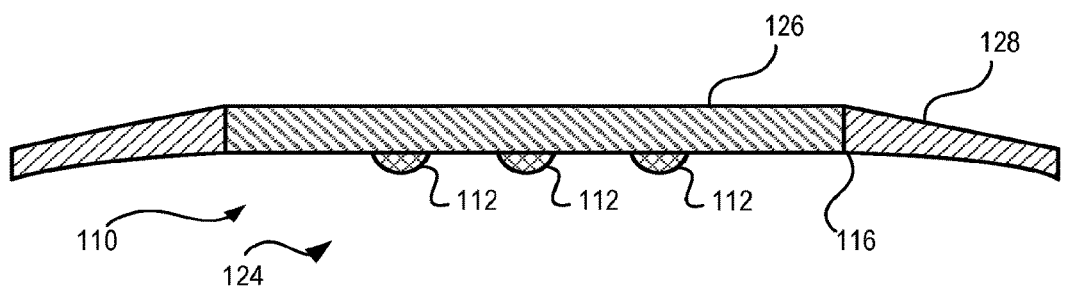
FIG. 6 illustrates a cross-section view of FIG. 5 taken along the line 6-6 of FIG. 5 in accordance with certain embodiments herein.

FIG. 5 illustrates an example front view of the body 110 having an inner portion 126 and an outer portion 128, and FIG. 6 illustrates a cross-section view of FIG. 5 taken along the line 6-6 of FIG. 5. For ease of understanding, additional internal features of the body 110 are omitted from FIGS. 5 and 6 (e.g., the lead 140 is omitted, as are internal wiring components connecting the lead to the electrodes 112). In the illustrated example, the outer portion 128 surrounds the perimeter of the inner portion 126 (e.g., the outer portion 128 circumferentially surrounds the inner portion 126). In other examples, the outer portion 128 can extend from (e.g., but need not necessarily surround) the inner portion 126. The outer portion 128 can include fixation features to facilitate attaching the body 110 to the oval window or the ossicular chain. The inner portion 126 and the outer portion 128 can be formed from the same or different materials. In examples, the outer portion 128 can be formed from a softer material than the material of the inner portion 126. In examples, the outer portion 128 has a decreased thickness compared to the inner portion 126. In an example, the inner portion 126 can have a region (e.g., extending from a top of the inner portion 126 to a bottom of the inner portion 126) having a thickness of approximately 3 mm or less, 2 mm or less, or 1 mm or less. The outer portion 128 can have a region (e.g., extending from a top of the outer portion 128 to a bottom of the outer portion 128) having a thickness of approximately 2 mm or less 1.5 mm or less, 1 mm or less, or 0.5 mm or less.

As can be seen in FIG. 6, the outer portion 128 can define a concavity 124 of the body 110. The electrodes 112 can be disposed within the concavity 124. In an example, the concavity 124 has a depth approximately equal to the height of the electrodes 112. In an example, the concavity 124 is configured to form a seal with the oval window, the oval window niche, the temporal bone, other tissue, or combinations thereof. In examples, the body 110 can act as a diaphragm that vibrates in response to vibrations conducted from the ossicular chain and conducts the vibrations to the oval window.

Figure 7:
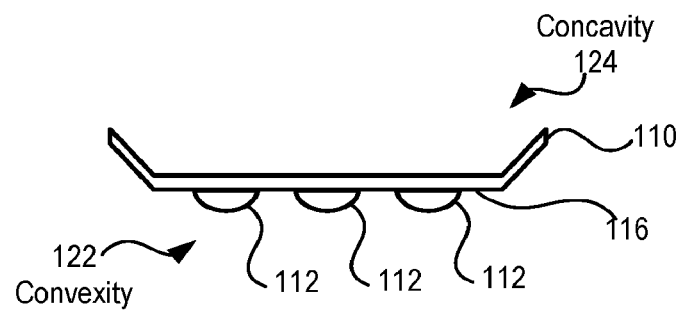
FIG. 7 illustrates an example side view of the body with electrodes disposed proximate a convex portion of the body having substantially straight sides in accordance with certain embodiments herein.
Figure 8:
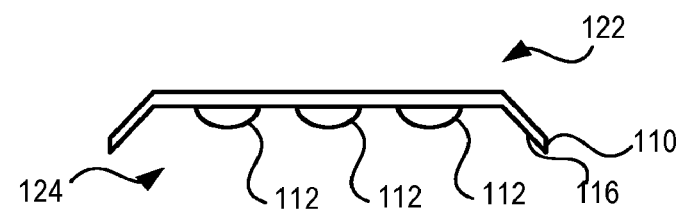
FIG. 8 illustrates an example side view of the body having electrodes disposed proximate a concave portion of the body having substantially straight sides in accordance with certain embodiments herein.

FIGS. 7 and 8 illustrate side views of an example body 110. In an example, the body 110 can have a shape like that of FIG. 7 or FIG. 8 in cross section along a width or a length of the body 110. As illustrated, the body 110 has a trapezoidal shape defining a concavity 124 and a convexity 122. The sides of the body 110 defining the concavity 124 and the convexity 122 are substantially straight. The base of the concavity 124 and convexity 122 are also substantially straight. FIG. 7 shows the electrodes 112 disposed at the convex portion of the body 110. In such an example, the concavity 124 can facilitate a connection between the body 110 and the ossicular chain. For example, the stapes can be configured to at least partially fit within the concavity 124. FIG. 8 shows the electrodes 112 disposed at the concave portion of the body 110. In an example, the concavity 124 can facilitate a connection between the body 110 and the oval window.

Figure 9:
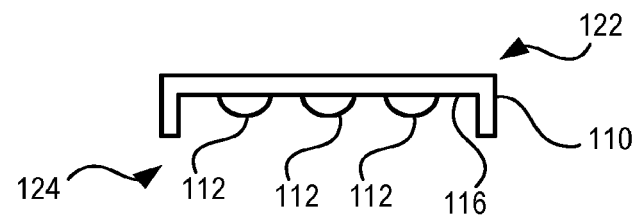
FIG. 9 illustrates an example side view of the body with a rectangular shape defining a concavity and a convexity in accordance with certain embodiments herein.

FIG. 9 illustrates a side view of an example body 110. In an example, the body 110 can have a shape like that of FIG. 9 in cross section. As illustrated, the body 110 has a rectangular shape defining a concavity 124 and a convexity 122. The sides of the body 110 defining the concavity 124 and the convexity 122 are substantially straight and are approximately perpendicular to a base of the concavity 124. The base of the concavity 124 and the base of the convexity 122 are also substantially straight. As illustrated, the electrodes 112 are disposed at the concavity 124 of the body 110. In another configuration, the electrodes 112 can be disposed at the convexity 122 of the body 110. In an example, the concavity 124 can facilitate a connection between the body 110 and the oval window.

Figure 10:
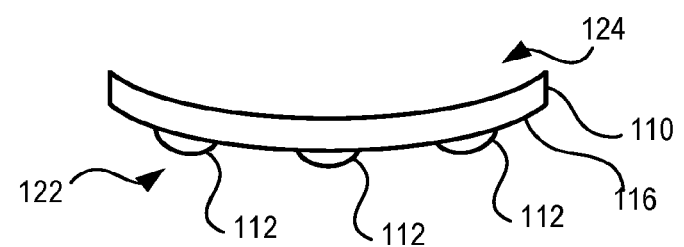
FIG. 10 illustrates an example side view of the body in a curved configuration with electrodes disposed proximate a convex portion of the body in accordance with certain embodiments herein.
Figure 11:
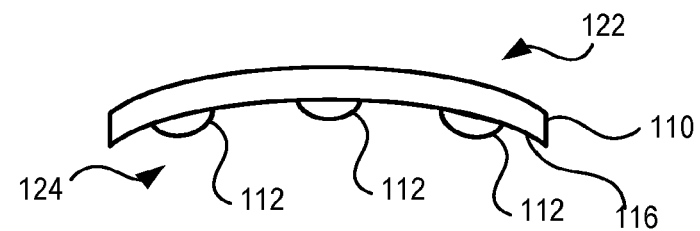
FIG. 11 illustrates an example side view of the body in a curved configuration with electrodes disposed proximate a concave portion of the body in accordance with certain embodiments herein.

FIGS. 10 and 11 illustrate example side view of an example body 110. In an example, the body 110 can have a shape like that of FIG. 10 or FIG. 11 in cross section. As illustrated, the body 110 has a curved shape defining a concavity 124 and a convexity 122. FIG. 10 shows the electrodes 112 disposed at the convexity 122 of the body 110. In such an example, the concavity 124 can facilitate a connection between the body 110 and the ossicular chain. For example, the stapes can be configured to at least partially fit within the concavity 124. FIG. 11 shows the electrodes 112 disposed at the concavity 124 of the body 110. In an example, the concavity 124 can facilitate a connection between the body 110 and the oval window.

Electrode Configurations

Just like the body 110 can take any of a variety of configurations, so too can the electrodes 112 take any number of shapes. Further, the electrodes 112 can be disposed in any of a variety of configurations on the body 110. Such shapes and configurations can be selected to facilitate targeting particular vestibular anatomy, such as otolith organs, when the body 110 is implanted. The electrodes 112 can be embedded in the body 110, can be disposed flush with a surface of the body 110, can extend a surface of the body 110 (e.g., such as perpendicular to the surface of the body 110 or at an angle relative to the surface), can take other configurations, or can take combinations of multiple configurations. The electrodes 112 can be affixed to the body 110. The electrodes 112 can also have any of a variety of different shapes or combinations of shapes. The electrodes 112 can be formed as part of an n-sided polygon or an n-pointed star polygon in shape or in cross-section where n is an integer three or greater. The electrodes 112 can each have a respective tip 114 having a particular configuration. For example, the tip 114 can be configured to resist penetrating oval window tissue, such as by having a blunt shape, thereby being configured to resist penetrating the oval window tissue when the body 110 is implanted proximate the oval window. In other examples, the tip 114 can be configured to penetrate the oval window tissue, such as by having a sharp shape configured to penetrate the oval window tissue when the body 110 is implanted proximate the oval window. In examples, the tip 114 can have a concavity or a convexity. Example configurations of the electrodes 112 are shown in FIGS. 12-20.

Figure 12:
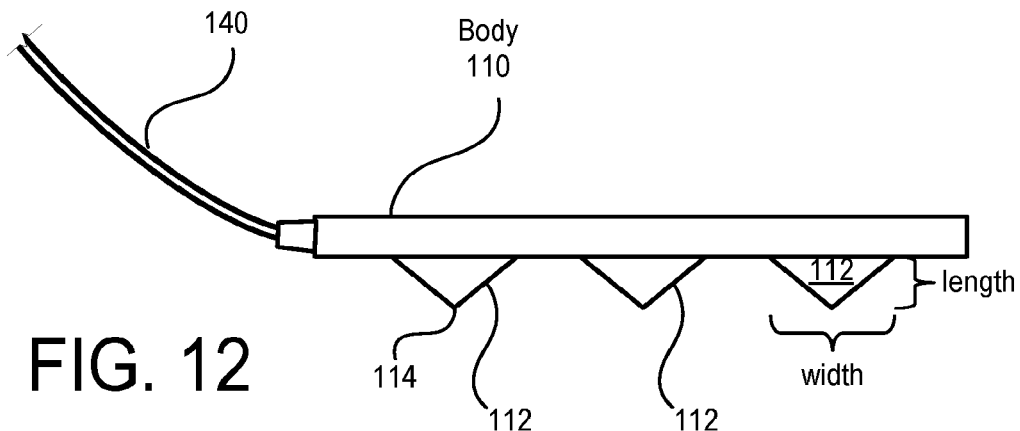
FIG. 12 illustrates an example side view of an example body with electrodes extending therefrom having a width greater than a length in accordance with certain embodiments herein.
Figure 13:
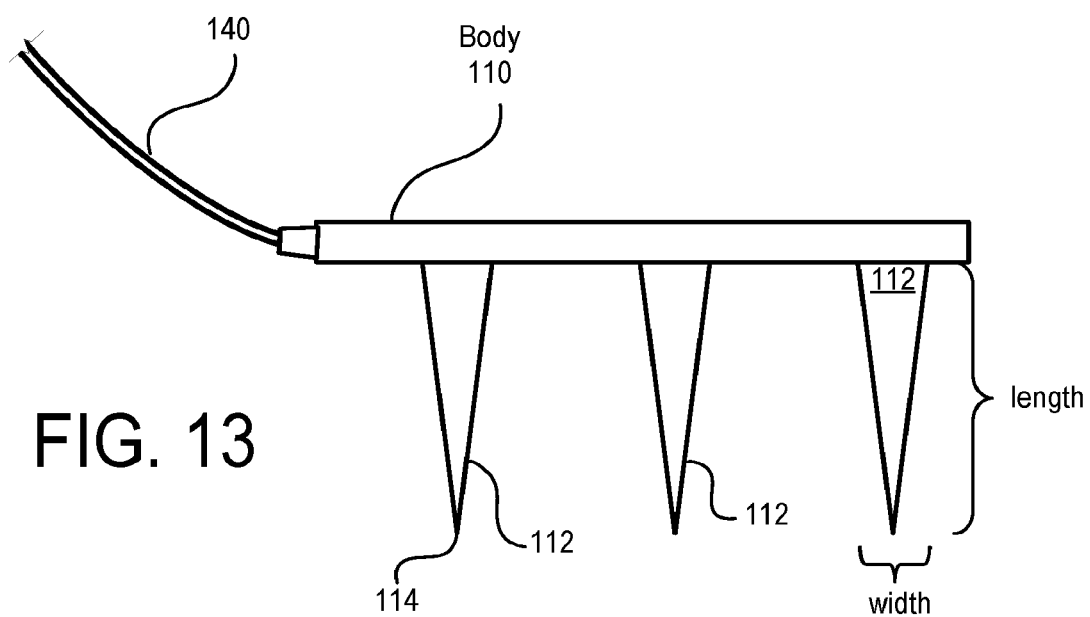
FIG. 13 illustrates an example side view of an example body with electrodes extending therefrom with a length greater than a width in accordance with certain embodiments herein.

FIGS. 12 and 13 illustrate side views of an example body 110 with electrodes 112 extending therefrom. In the illustrated configurations, the electrodes 112 have a triangular shape when viewed from at least one side. In examples, the electrodes 112 can be conical or shaped like pyramids having an n-sided base, where n is an integer three or greater (e.g., a triangular base pyramid, a square base pyramid, a pentagonal base pyramid, etc.). In examples, the electrodes 112 can be shaped like a triangular prism. The electrodes 112 are illustrated as having a pointed tip 114. Such a tip 114 can be relatively sharp and configured to penetrate tissue. In other examples, the tip 114 can be relatively rounded and configured to resist penetrating tissue. In FIG. 12, the electrodes 112 have a width greater than a length. In such a configuration, the electrodes 112 can be configured to resist penetrating tissue. In other examples, the electrodes 112 can be blade-like and have a relatively small depth such that the electrodes 112 are configured to penetrate tissue to a depth. In FIG. 13, the electrodes 112 have a length greater than their width. In such a configuration, the electrodes 112 can be configured to penetrate tissue. In an example, the length of the electrodes is selected to resist penetrating the oval window, damaging auditory anatomy, damaging vestibular anatomy, damaging other tissue, or combinations thereof. In an example, the length of the electrodes is selected to penetrate the oval window to a depth of 2.5 mm or less, 2 mm or less, 1.5 mm, or less, 1 mm or less, or 0.5 mm or less. In addition, although the figures are described with reference to electrodes 112, any one or more of the electrodes 112 described herein can be replaced with or operate as a sensor configured to obtain data relating to stimulation or other measurable data.

Figure 14:
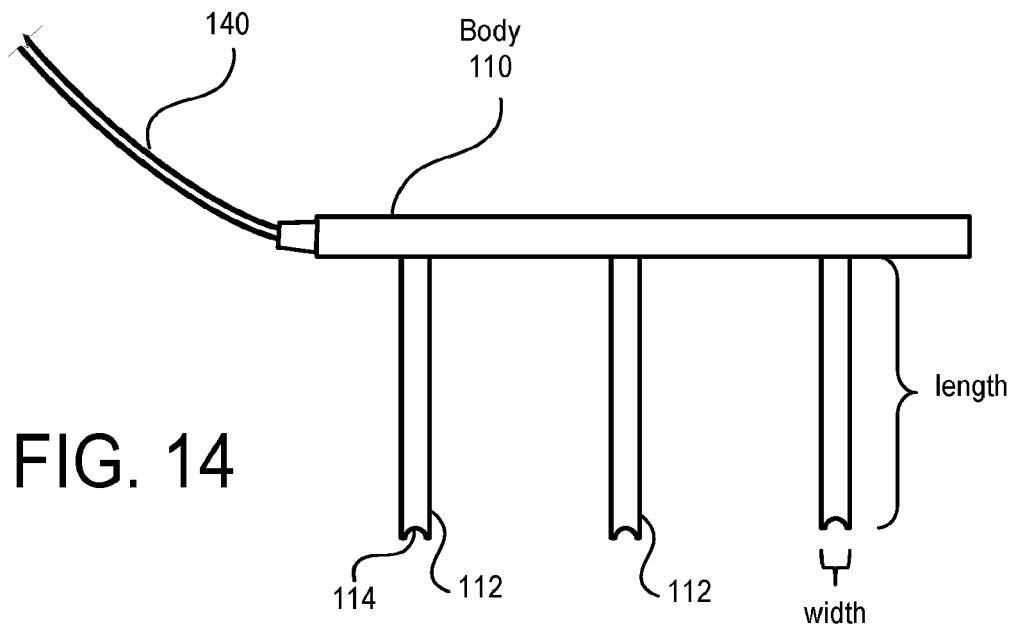
FIG. 14 illustrates a side view of an example body with electrodes extending therefrom tips with a convex shape in accordance with certain embodiments herein.

FIG. 14 illustrates a side view of an example body 110 with electrodes 112 extending therefrom. In the illustrated configuration, the electrodes 112 have a substantially rectangular shape when viewed from at least one side. The length of the electrodes 112 is longer than a width of the electrodes 112. In examples, the electrodes 112 can be cylindrical or rectangular. As illustrated, the tip 114 of the electrodes 112 has a convex shape. The tip 114 can take the form of a bident (e.g., has a bifurcated tip) with two tines extending from the body of the electrode. In examples, each of the two tines can be separate electrodes 112.

Figure 15:
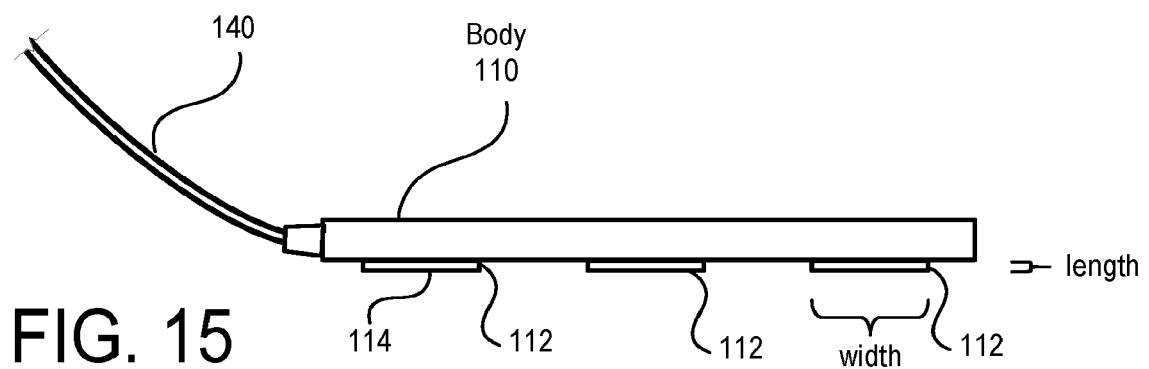
FIG. 15 illustrates a side view of an example body with electrodes extending therefrom having a flat tip in accordance with certain embodiments herein.

FIG. 15 illustrates a side view of an example body 110 with electrodes 112. In the illustrated configuration, the electrodes 112 have a substantially rectangular shape when viewed from at least one side. In examples, the electrodes 112 can be cylindrical or rectangular. The length of the electrodes is shorter than a width of the electrodes. As illustrated, the tip 114 of each of the electrodes 112 is flat. The flat tip 114 can resist penetrating the oval window, damaging auditory anatomy, damaging vestibular anatomy, damaging other tissue, or combinations thereof.

FIGS. 16-20 illustrate example arrangements of electrodes 112 relative to a surface of the body 110. The arrangement of the electrodes 112 can be selected to target vestibular anatomy with stimulation.

Figure 16:
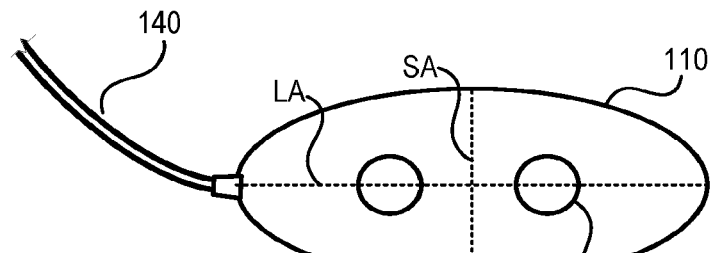
FIG. 16 illustrates a front view of an example body with two electrodes in accordance with certain embodiments herein.

FIG. 16 illustrates a front view of an example body 110 with two electrodes 112. In the illustrated configuration, the electrodes 112 are linearly disposed along the long axis of the body 110. The electrodes 112 are disposed in locations equidistant from the short axis of the body 110. In other examples, the electrodes 112 can be linearly disposed along the short axis of the body 110. In examples, the electrodes 112 can be disposed in a line rotated along any angle relative to the long axis.

Figure 17:
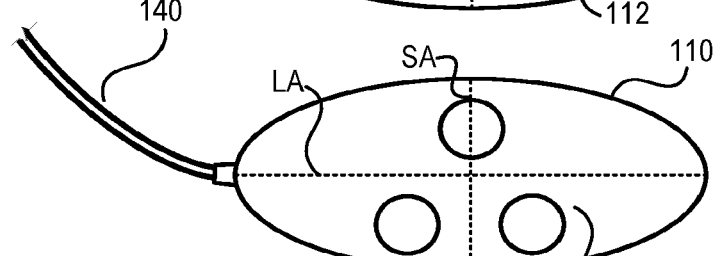
FIG. 17 illustrates a front view of an example body with three electrodes in accordance with certain embodiments herein.

FIG. 17 illustrates a front view of an example body 110 with three electrodes 112. In the illustrated configuration, the electrodes 112 are disposed in such a way to from vertexes of an equilateral triangle centered on the body 110 (e.g., an equilateral triangle centered where the long and short axes meet). The electrodes 112 can be disposed in such a way as to form any other kind of triangle on the body 110 (e.g., an isosceles triangle, a scalene triangle, a right tringle, an obtuse triangle, or an acute triangle). The triangle can be centered elsewhere on the body 110 and rotated to any angle (e.g., any angle θ, where θ is an integer between 0 and 360 degrees, inclusive) relative to the long axis.

Figure 18:
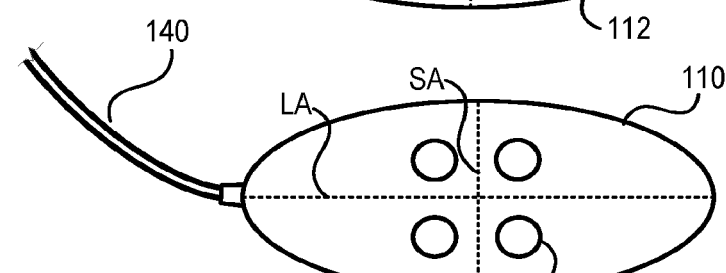
FIG. 18 illustrates a front view of an example body with four electrodes in accordance with certain embodiments herein.

FIG. 18 illustrates a front view of an example body 110 with four electrodes 112. In the illustrated configuration, the electrodes 112 are disposed in such a way to from vertexes of a square centered on the body 110. The electrodes 112 can be disposed in such a way as to form any other kind of rhombus on the body 110 (e.g., rectangles, squares, parallelograms or trapezoids). The rhombus can be centered elsewhere on the body 110 and can be rotated to any angle (e.g., any angle θ, where θ is an integer between 0 and 360 degrees, inclusive) relative to the long axis.

Figure 19:
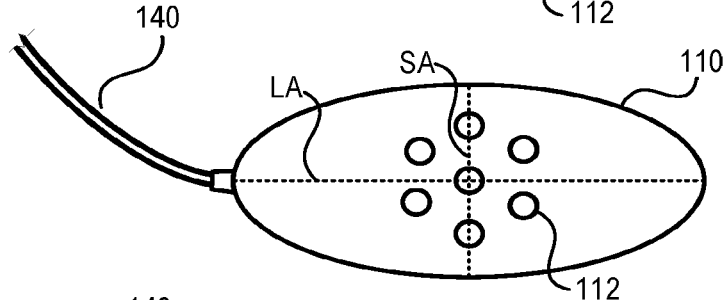
FIG. 19 illustrates a front view of an example body with seven electrodes in accordance with certain embodiments herein.

FIG. 19 illustrates a front view of an example body 110 with seven electrodes 112. In the illustrated configuration, the electrodes 112 are disposed in such a way to from vertexes of a hexagon centered on the body 110 with an additional electrode 112 disposed at the center of the hexagon. While the illustrated electrodes 112 are disposed to form an equilateral and equiangular hexagon, the electrodes 112 can be disposed to form a non-equilateral and non-equiangular hexagon. The illustrated hexagon is centered at a center of the body 110 but can be centered elsewhere on the body 110 and can be rotated to any angle (e.g., any angle θ, where θ is an integer between 0 and 360 degrees, inclusive) relative to the long axis.

Figure 20:
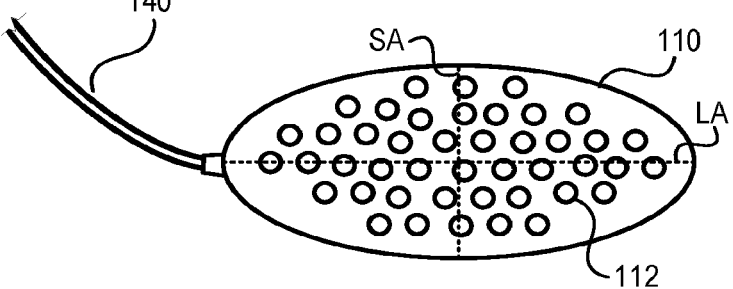
FIG. 20 illustrates a front view of an example body with many electrodes in accordance with certain embodiments herein.

FIG. 20 illustrates a front view of an example body 110 with many electrodes 112. The electrodes 112 can be disposed on the body in any of a variety of ways, such as at vertices of an n-sided polygon where n is an integer three or greater. The electrodes 112 can be disposed in other locations as well. For example, the electrodes 112 can be disposed to fill a region of the body 110 with electrodes a predetermined distance apart. In an example, the total surface area of the electrodes visible in a front view is greater than a total surface area of the body 110 visible in the front view.

As described above, the shapes and configurations of the electrodes 112 and the body 110 can be selected to facilitate targeting particular vestibular anatomy, such as otolith organs, when the body 110 is implanted. In many implementations, the body 110 further includes a coupling to facilitate the implantation of the body 110, positioning of the electrodes 112, and the targeting of vestibular anatomy.

Coupling

Examples of the vestibular stimulation prosthesis 100 can further include a coupling 400 configured to couple the body 110 with tissue of the recipient (e.g., the temporal bone or a bone of the recipient's auditory ossicles, such as one or more of the malleus, the incus, and the stapes). The coupling 400 can be further configured to receive and conduct vibrations from the ossicular chain to the body 110 for transmission to the oval window.

Figure 21:
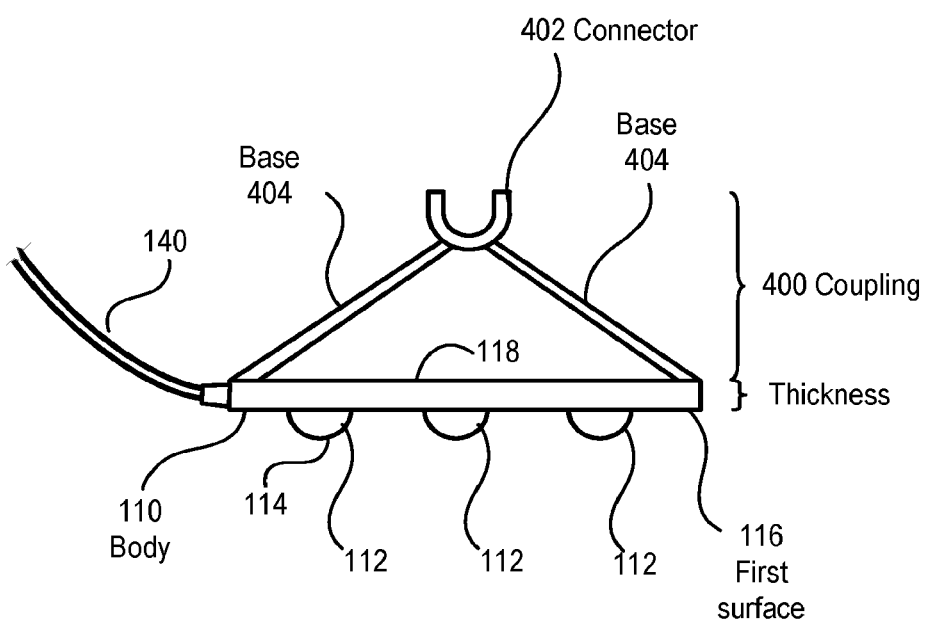
FIG. 21 illustrates a side view of an example body having a coupling extending from the second surface of the body.

FIG. 21 illustrates a side view of an example body 110 having a coupling 400 extending from the second surface 118 of the body 110. The coupling 400 can be a component configured to couple the body 110 with a bone of the recipient's auditory ossicles. The coupling 400 can take any of a variety of forms. In the illustrated configuration, the coupling 400 includes a connector 402 and one or more bases 404.

The connector 402 can be the portion of the coupling 400 that couples with the bone or other tissue of the recipient. The connector 402 can take any of a variety of different forms, such as one or more clips, screws, hooks, clamps, fasteners, adhesives, cements (e.g., bone cement), other kinds of couplings, or combinations thereof. In an example, the connector 402 comprises a metal, such as titanium.

The base 404 can be the portion of the coupling 400 that links the body 110 with the connector 402. In examples, the base 404 can facilitate the positioning of the connector proximate tissue (e.g., the ossicular chain) with the first surface 116 of the body 110 positioned proximate the oval window. In examples, the base 404 is adjustable to facilitate such positioning. For instance, the angle between the base 404 and the connector can be adjustable. Likewise, the angle between the base 404 and the body 110 can also be adjustable. Further, a length of the base 404 can be adjustable. Further still, the base 404 can include an adjustable or fixed bend to facilitate angling the body 110 relative to the connector 402. In some examples, the base 404 is sized and shaped to mimic one or more portions of the ossicular chain. In some examples, the base 404 is configured to conduct vibrations form the connector 402 to the body 110 for transmission to the oval window. In an example, the connector 402 comprises an elastomer, such as silicone.

Figure 22:
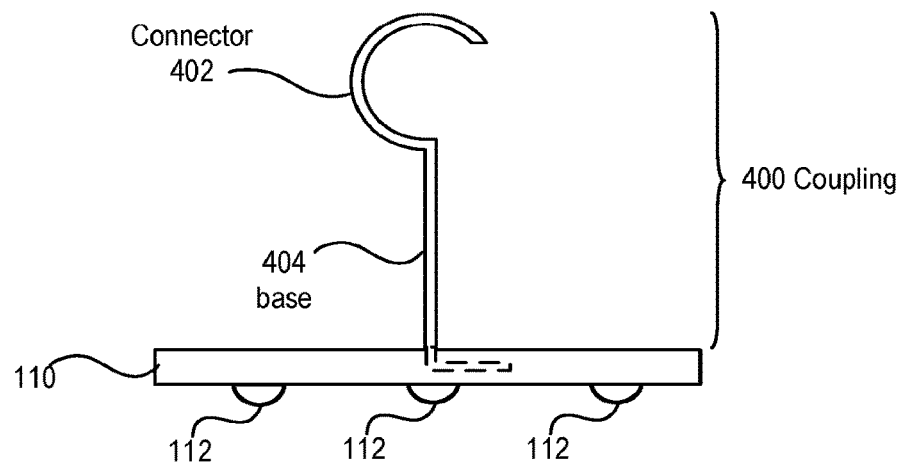
FIG. 22 illustrates an example coupling having a form of a hook and a base in accordance with certain embodiments herein.

FIG. 22 illustrates an example coupling 400. In the illustrated configuration, the coupling 400 has a connector 402 in the form of a hook and a base 404 in the form of an elongate section extending from the hook and terminating in the body 110. In an example, the connector 402 and the base can be integral with each other. The connector 402 and the base 404 can be formed from the same material, such as a metal (e.g., titanium). As illustrated, the base 404 extends from the second surface 118 and is substantially perpendicular to the second surface 118. The base 404 extends from a middle of the body 110 but could be disposed elsewhere. The hook of the connector can be configured to attach directly to a bone of the ossicular chain or a fixation element coupled to the bone (e.g., a screw disposed within the bone). In examples, the hook can be configured to pierce into the bone. The hook can form its own path through the bone or follow a pre-excavated path.

Figure 23:
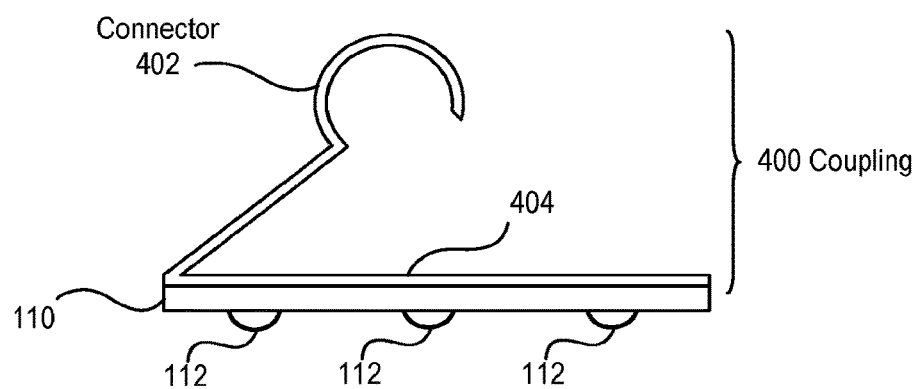
FIG. 23 illustrates an example coupling having a form of a hook and a base with the base in the form of an elongate section extending from the hook in accordance with certain embodiments herein.

FIG. 23 illustrates an example coupling 400. As in FIG. 22, the coupling 400 has a connector 402 in the form of a hook and a base 404 in the form of an elongate section extending from the hook. But in the configuration illustrated in FIG. 23, the base 404 extends from an area proximate an edge of the body 110 at a non-perpendicular angle to the body 110. As illustrated, the base 404 further includes a section extending from the edge of the body 110 along at least a portion of the body 110. In the illustrated configuration, the base 404 extends along the second surface 118 without being disposed within the body 110. In an example, the base 404 can be welded, adhered, or otherwise fastened to the body 110 without the base 404 being disposed within the body 110.

Figure 24:
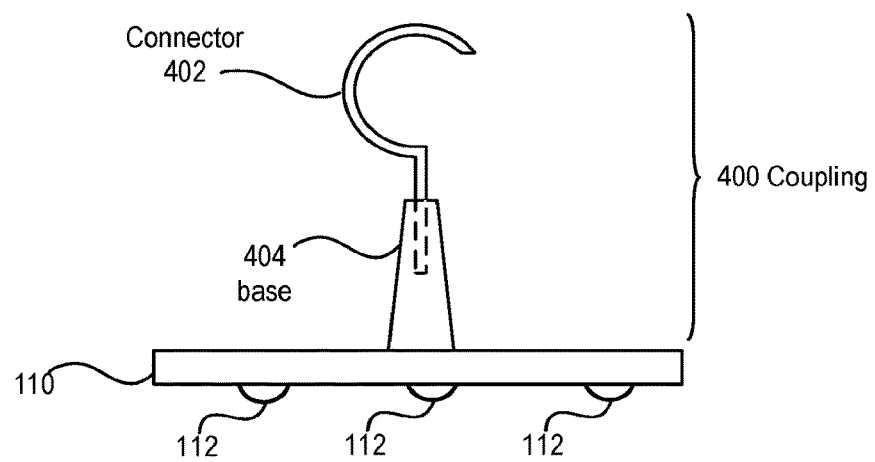
FIG. 24 illustrates an example coupling having a form of a hook and a base with the base in the form of a pedestal in accordance with certain embodiments herein.

FIG. 24 illustrates an example coupling 400. As in FIGS. 22 and 23, the coupling 400 has a connector 402 in the form of a hook. But in the configuration illustrated in FIG. 24, the base 404 takes the form of a pedestal extending from the second surface 118. As illustrated, the base 404 is trapezoidal or frustoconical but can take other forms. Further, a section of the connector 402 extends into the base 404 for support. In an example, the base 404 can be integral with the body 110 or discrete from the body. In an example, the base 404 can be formed from the same material as the body 110. In an example, the connector 402 is formed from a metal (e.g., titanium) and the base 404 is formed from an elastomer (e.g., silicone).

Figure 25:
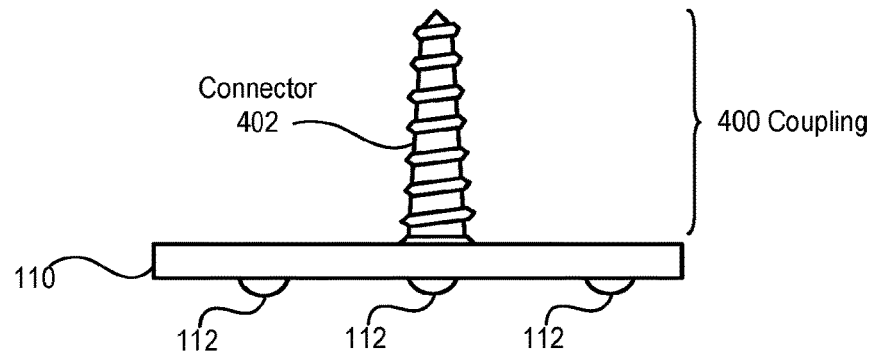
FIG. 25 illustrates an example coupling having a form of a screw. in accordance with certain embodiments herein

FIG. 25 illustrates an example coupling 400. In the illustrated configuration, the coupling has a connector 402 in the form of a screw extending from the body 110. In an example, such a configuration can be considered to lack a base 404.

Figure 26:
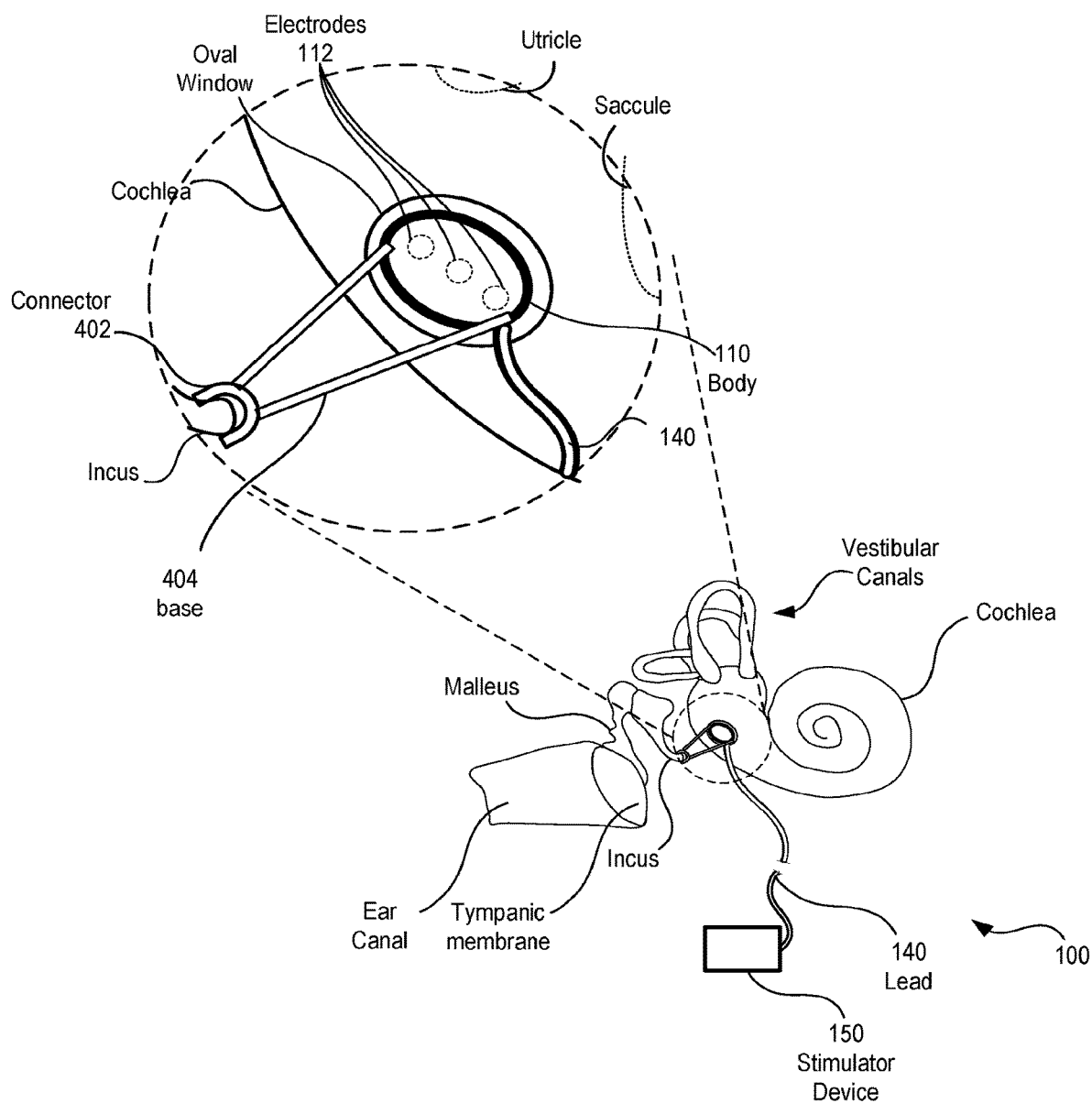
FIG. 26 illustrates an embodiment of an ossicular-bone-replacement configuration of the body in accordance with certain embodiments herein.

FIG. 26 illustrates an embodiment of an ossicular-bone-replacement configuration of the body 110. In particular, as illustrated, the body 110 is implanted in the ossicular chain replacing the stapes (but in one or more other examples, one or more other bones of the ossicular chain can be partially or wholly replaced). The body 110 includes a coupling 400 sized and shaped to replace the stapes. In particular, the coupling 400 is sized to place the electrodes 112 proximate the oval window when the body 110 is implanted with the connector 402 of the coupling connected to the incus. For instance, the base 404 can be sized and shaped to reach from the incus to the oval window. In this configuration, the body 110 can be configured to conduct vibrations from the incus to the oval window.

Example Processes

Figure 27:
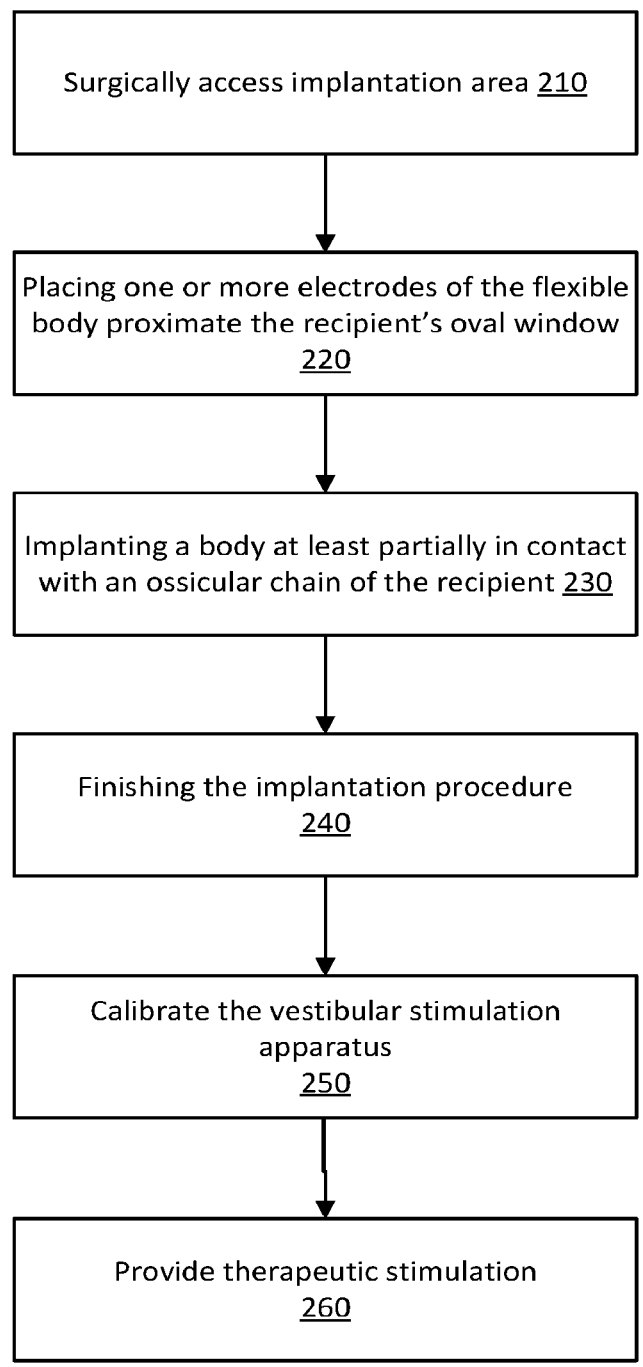
FIG. 27 illustrates an example process for implanting and using a vestibular stimulation prosthesis in accordance with certain embodiments herein.
Figure 28:
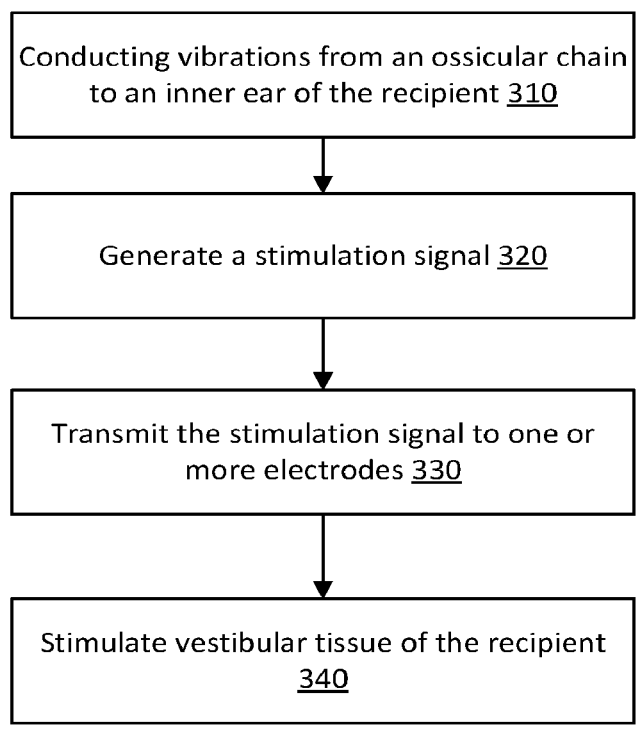
FIG. 28 illustrates an example process for stimulating vestibular tissue of a recipient in accordance with certain embodiments herein.

FIG. 27 illustrates an example process 200 for implanting and using a vestibular stimulation prosthesis. The process 200 can begin with operation 210.

Operation 210 includes surgically accessing an implantation area in a recipient. For instance, a clinician can form an incision in tissue proximate a location where the vestibular stimulation prosthesis 100 is to be implanted and remove tissue to expose an implantation area. The incision can be sized and shaped to allow for the performance of operations 220 and 230 through the incision. In some examples, surgically accessing the implantation area includes performing a mastoidectomy. The operation can further include enlarging a posterior tympanotomy, which can include exposing the oval window, such as by enlarging superiorly the posterior tympanotomy. In some examples, surgically accessing the implantation area includes identifying the stapes, as well as the anterior and posterior crura of the stapes and the footplate of the stapes, which contacts the oval window. The facial nerve of the recipient proximate the oval window can also be identified.

In some examples, operation 210 further includes excavating ossicular chain tissue form a location for implanting a body 110. For instance, using an excavating tool (e.g., a carbon dioxide laser) or a surgical drill, some or all of the footplate of the stapes is removed to make room for the body 110. In some instances, the incus is removed to make room to place the body 110. In some instances, the ligaments of the footplate are kept in position proximate the oval window. Following operation 210, the flow can move to one or both of operation 220 and operation 230.

Operation 220 includes placing one or more electrodes 112 of the body 110 proximate the recipient's oval window. This can include placing the body 110 partially or entirely on the oval window of the recipient. In some examples, the body 110 contacts the temporal bone surrounding the oval window. The placing of the electrodes 112 can include placing the electrodes such that they do or do not pierce the oval window. In examples, the electrodes 112 are inserted through the oval window to a depth of 2.5 mm or less, 2 mm or less, 1.5 mm, or less, 1 mm or less, 0.5 mm or less. In some examples, the electrodes 112 are inserted into the oval window to a depth less than a depth to which auditory and vestibular anatomy is damaged by the electrodes 112 during insertion (e.g., damaged in a way to cause loss of hearing or vestibular function, respectively). In some examples, a portion of the body 110 at which the electrodes 112 are disposed is positioned such that the electrodes face the area where the recipient's otolith organs are believed to be disposed.

Operation 230 includes implanting a body 110 at least partially in contact with an ossicular chain of the recipient. Placing the body 110 in contact with the ossicular chain can include connecting the body 110 to one or more of the bones of the recipient's ossicular chain. This can include connecting the coupling 400 to the bone. In addition, in some recipients, the facial nerve may impinge on the implantation area. In such instances, a material (e.g., foam) can be placed between the implanted body 110 and the impinging facial nerve.

Following operations 220 and 230, the flow can move to operation 240. Operation 240 includes finishing the implantation procedure. Finishing the implantation procedure can include closing one or more incisions made to access the implantation area. Following operation 240, the flow can move to operation 250.

Operation 250 includes calibrating the vestibular stimulation prosthesis 100. This operation can be performed at various times and can be performed various numbers of times. For instance, the vestibular stimulation prosthesis 100 can be calibrated before or during implantation, such as to confirm appropriate functioning of the vestibular stimulation prosthesis 100 prior to implantation or to confirm appropriate placement of the electrodes 112 prior to operation 240. The calibration can include performing vestibular response telemetry. Vestibular response telemetry can be used to confirm that one or more of the electrodes 112 are able to provide appropriate stimulation (e.g., to the vestibular tissue, such as nerve tissue). The vestibular response telemetry can include providing stimulation and measuring a response to the stimulation to determine whether placement of the electrodes 112 is appropriate. If the placement is inappropriate, the body 110 can be repositioned. In some examples, the vestibular response telemetry is used to determine which one or more electrodes of the one or more electrodes 112 is best able to stimulate target anatomy. Those one or more electrodes best able to stimulate the target anatomy can be selected as the electrodes to provide stimulation and the remaining electrodes can be (at least initially) deactivated. In many examples, additional calibration is performed subsequent to the finishing of the implantation procedure.

In examples, at least one month after implantation, the performance of the vestibular stimulation prosthesis 100 is tested. In an example, the recipient is asked to stand with their legs together and looking forward. Stimulation is provided by the vestibular stimulation system. The stimulation level of the stimulation provided can begin at a relatively low level. The stimulation level of the stimulation provided by the vestibular stimulation prosthesis 100 is then increased while the recipient's posture is poor or exhibits signs of poor balance (e.g., the recipient is swaying or shaking). When the recipient's posture and/or balance improves, the increase to the stimulation is stopped. Further, the recipient's subjective reports of their own perception of balance can used to determine whether to stop increasing stimulation levels. The stimulation level provided by the vestibular stimulation prosthesis 100 that ameliorates the recipient's balance can then be set such that the vestibular stimulation prosthesis 100 provides that level of stimulation going forward. The stimulation level can include a rate of stimulation. In examples, the stimulation rate is within the range of 200 Hz to 1000 Hz. Other levels are also possible. Further, while the electrodes 112 can be configured to provide a same stimulation rate or level, they need not. For instance, one electrode 112 can provide stimulation at a rate of 900 Hz and other electrodes 112 can provide stimulation at a rate of 500 Hz. Following operation 250, the flow can move to operation 260.

Operation 260 includes providing therapeutic stimulation with the vestibular stimulation prosthesis 100. This operation 260 can include providing therapeutic stimulation to the vestibular system, as well as conducting sound vibrations to the oval window or associated tissue. After calibration, the vestibular stimulation prosthesis 100 can provide therapeutic stimulation to the recipient. This can include the vestibular stimulation prosthesis 100 providing stimulation according to a schedule generated based at least in part on the calibration of the vestibular stimulation prosthesis. Providing the therapeutic stimulation can include providing stimulation continuously to the recipient. Providing the therapeutic stimulation can include providing the stimulation periodically. Providing the stimulation periodically can include providing an amount of stimulation every approximately forty minutes to one hour for a therapeutic amount of time.

In an example, the operation 260 includes one or more operations described in relation to FIG. 27, which describes an example process 300 stimulating vestibular tissue of a recipient. In an example, the process 300 begins with operation 310.

Operation 310 includes conducting vibrations from an ossicular chain to an inner ear of the recipient. In an example, the body 110 of the vestibular stimulation prosthesis 100 can conduct the vibrations from a bone of the ossicular chain (e.g., incus, malleus, or stapes). A connector 402 of the body can connect to the bone and receive the vibrations. The connector 402 can conduct the vibrations to the base 404. The base 404 can conduct the vibrations to the portion of the body 110 that contacts the oval window. In some examples, the vibrations are conducted via the one or more electrodes 112 to the oval window. In some examples, the vestibular stimulation prosthesis 100 can attenuate the vibrations received from the ossicular chain. The attenuation can, in some examples, cause a measurable (but not necessarily total) hearing loss in the recipient.

The method further includes operation 320. In the illustrated example, operation 320 follows operation 310, but in most implementations the operations occur without respect to the timing of the other. For example operation 310 can occur passively while the vestibular stimulation prosthesis 100 is implanted and operation 320 can occur according to a schedule.

Operation 320 includes generating a stimulation signal. In examples, the stimulation signal is generated by the stimulator 156. The stimulation signal can be, for example, an electrical stimulation signal. The stimulator 156 can generate the stimulation signal based on a schedule or program. In other examples, the stimulator 156 generates the stimulation signal based on input from another component of the stimulator device 150 (e.g., a processor thereof) or based on input from another device of the vestibular stimulation prosthesis 100 (e.g., an external device). Generating the stimulation signal can include generating a stimulation signal selected to treat a vestibular condition of the recipient. Following operation 320, the flow can move to operation 330.

Operation 330 includes transmitting the stimulation signal to the one or more electrodes 112. The transmitting can include transmitting the stimulation signal through a wired (e.g., via the lead 140) or wireless connection between the stimulator 156 and the one or more electrodes 112. In examples, a same stimulation signal can be sent to all of the electrodes 112. In other examples, different stimulation signals are applied to different electrodes. In some examples, certain of the electrodes can be selectively activated to target stimulation at a particular anatomical location (e.g., to target vestibular anatomy through the oval window). In some examples, the one or more electrodes 112 are selectively activated or deactivated. Following operation 330, the flow can move to operation 340.

Operation 340 includes stimulating vestibular tissue of the recipient. For example, the one or more electrodes 112 can provide the stimulation using the received stimulation signal. In examples the vestibular tissue stimulated includes one or more of the vestibular canals or one or more of the otolith organs (e.g., the utricle and the saccule). In examples, stimulating vestibular tissue includes stimulating one or more nerves associated with the vestibular system, such as the vestibulocochlear nerve. The operation can include providing electrical stimulation through an oval window of the recipient.

Reference Electrodes

Disclosed examples can also include a reference electrode system 500 for affixing a reference electrode to bony structure of middle ear anatomy. The use of a reference electrode in the middle ear with the vestibular stimulation prostheses 100 described herein can provide advantages. For example, the use of the reference electrode system 500 can facilitate current steering, (e.g., so that stimulation currents can be more precisely applied to their intended targets). Although described herein in the context of a vestibular stimulation system, the reference electrodes described herein can be used in addition to or instead of the reference electrodes for inner ear stimulation devices described in U.S. 2012/0078337, entitled "Reference electrodes for inner ear stimulation devices", which is hereby incorporated herein by reference for any and all purposes. Reference electrodes for heritage inner ear stimulation devices have commonly been affixed between the skull and the muscle and are not implanted within the middle ear cavity.

Figure 29:
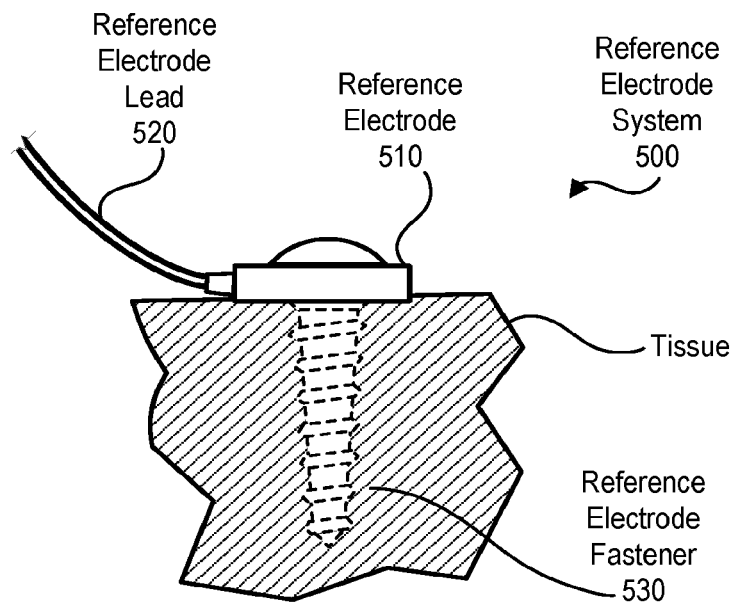
FIG. 29 illustrates a side view of an example reference electrode system affixed to tissue in accordance with certain embodiments herein.

FIG. 29 illustrates a side view of an example reference electrode system 500 affixed to tissue. The illustrated reference electrode system 500 includes a reference electrode 510, a reference electrode lead 520 coupled to and extending from the reference electrode 510, and a reference electrode fastener 530 that fastens the reference electrode 510 to tissue. The reference electrode lead 520 can be a cable that electrically connects the reference electrode 510 to another component (e.g., the stimulator device 150). The tissue can be any of a variety of tissue. In an example the tissue is tissue of the middle ear or inner ear. The tissue can be a bone of the ossicular chain or temporal bone located within the middle ear.

The reference electrode fastener 530 is a component configured to fasten the reference electrode 510 to tissue. The fastener 530 can take any of a variety of different forms, such as one or more clips, screws, hooks, clamps, fasteners, adhesives, cements (e.g., bone cement), other kinds of couplings, or combinations thereof. In an example, the fastener 530 comprises a metal, such as titanium. In some examples the fastener 530 is conductive to facilitate the performance of the reference electrode 510. In other examples, the fastener 530 is non-conductive. The reference electrode fastener 530 is a screw that passes through the reference electrode (e.g., through an opening defined by the reference electrode 510). The shaft of the screw extends primarily on a first tide of the reference electrode 510 (e.g., below the reference electrode 510 in the illustrated configuration) and the head of the screw extends primarily on a second surface of the reference electrode (e.g., above the reference electrode in the illustrated configuration). In examples, the reference electrode fastener 530 can be configured to form a path into tissue (e.g., by having a self-tapping feature or a piercing structure). In examples, the reference electrode fastener 530 is configured to follow a pre-formed hole through tissue (e.g., a path formed via a drill) formed into the target tissue.

The reference electrode 510 can be an electrode configured to act as a reference electrode for a device or system, such as the vestibular stimulation prosthesis 100. The reference electrode 510 can take any number of shapes and can be disposed in any of a variety of configurations. Such shapes and configurations can be selected to facilitate contacting particular tissue, such as middle or inner ear anatomy, when the reference electrode system 500 is implanted. The reference electrode 510 can have any of a variety of different shapes or combinations of shapes. The reference electrode 510 can be formed as part of an n-sided polygon or an n-pointed star polygon in shape or in cross-section. The reference electrode 510 can include one or more structural features, such as protrusions, concavities, convexities, tips, other structures, or combinations thereof. For example, the reference electrode 510 can be configured to resist or promote penetrating of tissue, such as by having a blunt shape or a sharp structure, respectively. Example configurations of the reference electrode 510 are shown in FIGS. 30-38.

Figure 30:
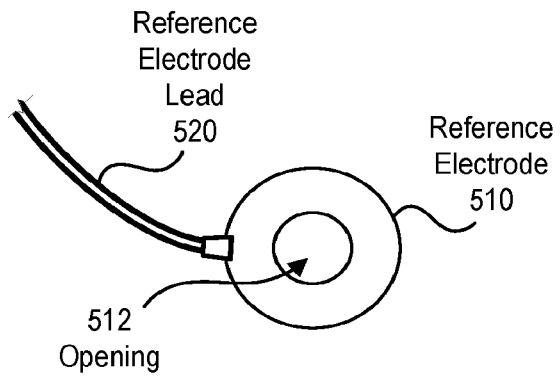
FIG. 30 illustrates a first example top view or bottom of the reference electrode system of FIG. 29 with the tissue and reference electrode fastener omitted in accordance with certain embodiments herein.

FIG. 30 illustrates a first example top or bottom view of the reference electrode system 500 of FIG. 29 with the tissue and the reference electrode fastener omitted 530. The illustrated reference electrode 510 defines an opening 512. The opening 512 can be a region lacking material. The opening 512 can be sized and shaped to be configured to receive the reference electrode fastener 530. For example, as illustrated, the reference electrode 510 has a washer shape with the opening 512 being an area through which a fastening screw can pass to fasten the reference electrode to tissue. As illustrated, the opening 512 is substantially centered in the reference electrode 510 and is surrounded by the reference electrode 510 on all sides when viewed down an axis of the opening 512.

Figure 31:
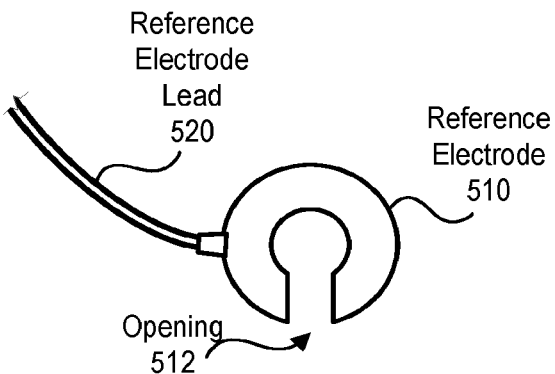
FIG. 31 illustrates a second example top view or bottom of the reference electrode system of FIG. 29 with the tissue and reference electrode fastener omitted in accordance with certain embodiments herein.

FIG. 31 illustrates a second example top or bottom view of the reference electrode system 500 of FIG. 29 with the tissue and the reference electrode fastener omitted 530. Like the reference electrode 510 of FIG. 30, the reference electrode 510 illustrated in FIG. 31 defines an opening 512. But this opening 512 is not completely surrounded by the reference electrode 510 on all sides when viewed down an axis of the opening. In the illustrated configuration, the reference electrode 510 is U-shaped. This configuration of the electrode 510 can facilitate the reference electrode 510 being slipped onto an existing reference electrode fastener or clipping the reference electrode 510 onto existing anatomy.

Figure 32:
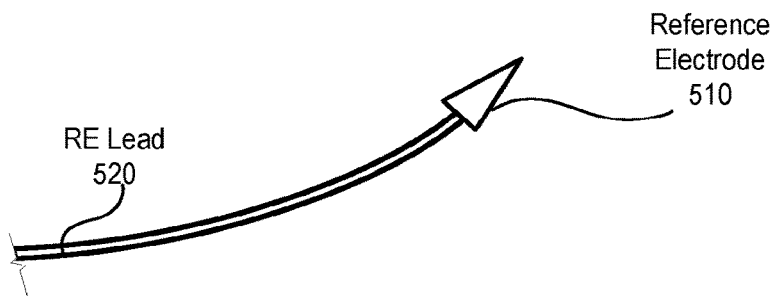
FIG. 32 illustrates an example implementation of reference electrode having a triangular shape in accordance with certain embodiments herein.

FIG. 32 illustrates an example implementation of reference electrode 510 having a triangular shape. The reference electrode 510 can have a point configured to pierce tissue. The triangular shape can be configured to pierce tissue during implantation of the reference electrode 510 to facilitate affixing the reference electrode 510 in tissue.

Figure 33:
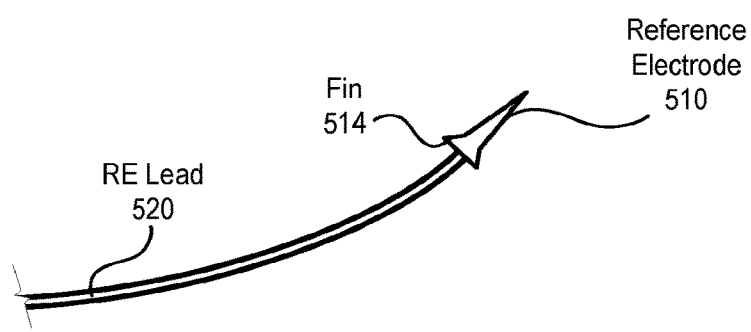
FIG. 33 illustrates an example implementation of reference electrode having an arrowhead-like shape in accordance with certain embodiments herein.

FIG. 33 illustrates an example implementation of reference electrode 510 having an arrowhead-like shape. The reference electrode 510 is triangular in shape. The reference electrode 510 can have a point configured to pierce tissue. The illustrated reference electrode 510 further includes one or more fins 514 at a proximal region of the reference electrode 510. The fins 514 can be configured to pierce or slice tissue during implantation of the reference electrode 510 to facilitate affixing the reference electrode 510 in tissue.

Figure 34:
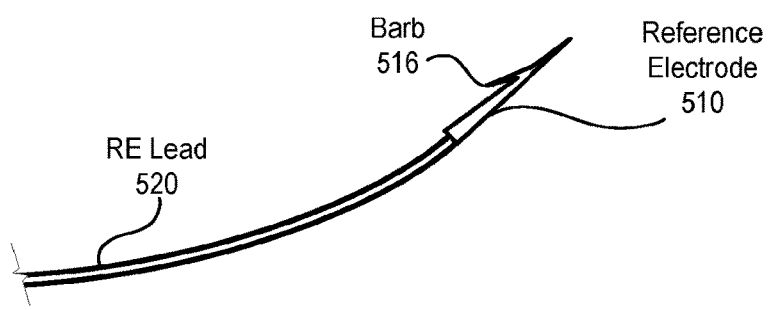
FIG. 34 illustrates an example implementation of reference electrode having a harpoon-tip-like shape in accordance with certain embodiments herein.

FIG. 34 illustrates an example implementation of reference electrode 510 having a harpoon-tip-like shape. The reference electrode 510 is triangular in shape with a point configured to pierce tissue. The illustrated reference electrode 510 further includes one or more barbs 516 extending proximally from a region near a tip of the reference electrode. The one or more barbs 516 can be configured to resist the removal of the reference electrode and thereby facilitate affixing the reference electrode 510 in tissue.

Figure 35:
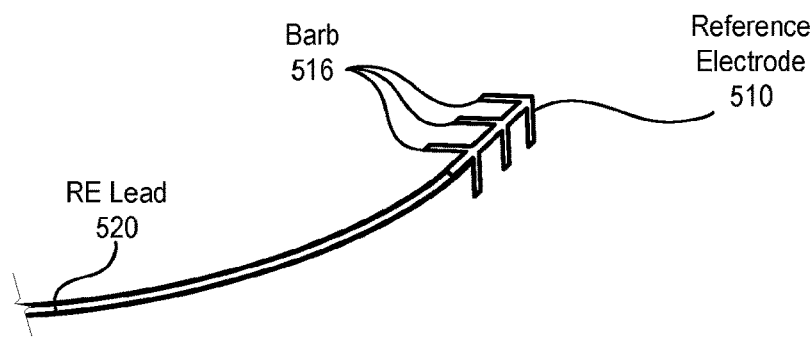
FIG. 35 illustrates an example implementation of reference electrode having a barbed-arrowhead-like shape in accordance with certain embodiments herein.

FIG. 35 illustrates an example implementation of reference electrode 510 having a barbed-arrowhead-like shape. The reference electrode 510 is triangular in shape with a point configured to pierce tissue. The illustrated reference electrode 510 further includes a plurality of rows of barbs 516 extending proximally from a region near a tip of the reference electrode. The one or more barbs 516 can be configured to resist the removal of the reference electrode and thereby facilitate affixing the reference electrode 510 in tissue.

Figure 36:
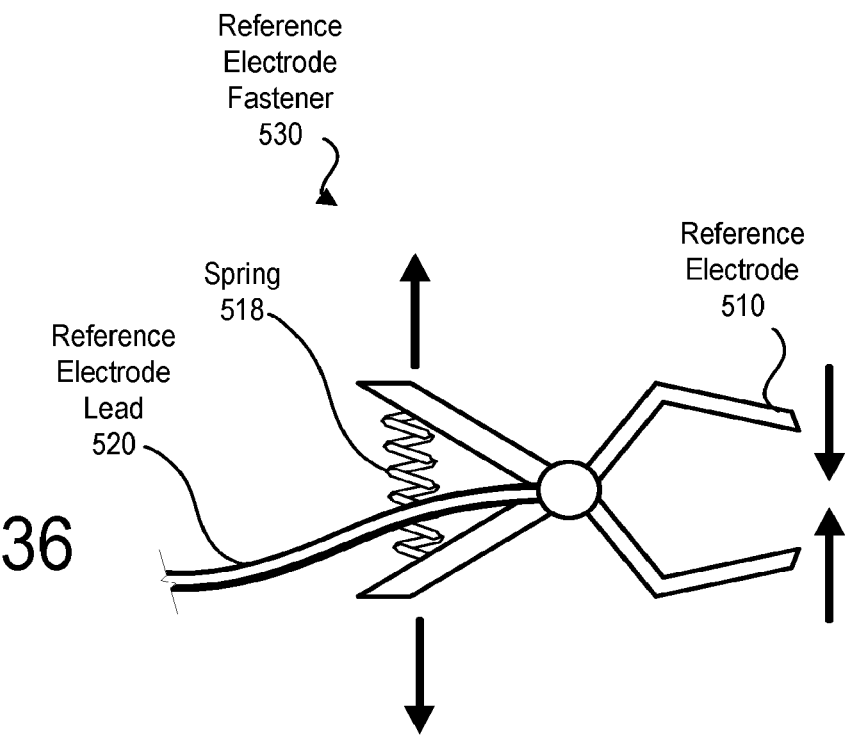
FIG. 36 illustrates an example implementation of a reference electrode having a reference electrode fastener configured as a clip in accordance with certain embodiments herein.

FIG. 36 illustrates an example implementation of a reference electrode 510 having a reference electrode fastener 530 configured as a clip. For example, the reference electrode fastener 530 can clip the reference electrode 510 to target anatomy. As illustrated, the reference electrode fastener 530 includes a spring 518 that forces apart a proximal portion of the reference electrode fastener 530, which forces together a distal portion of the fastener 530 at which the reference electrode 510 is disposed. The reference electrode fastener 530 can have a resting closed state. For instance, absent an outside force, the spring 518 causes the distal portion of the fastener 530 to close together. A clinician can force apart the distal portion by pressing the proximal portion of the fastener 530 together.

Figure 37:
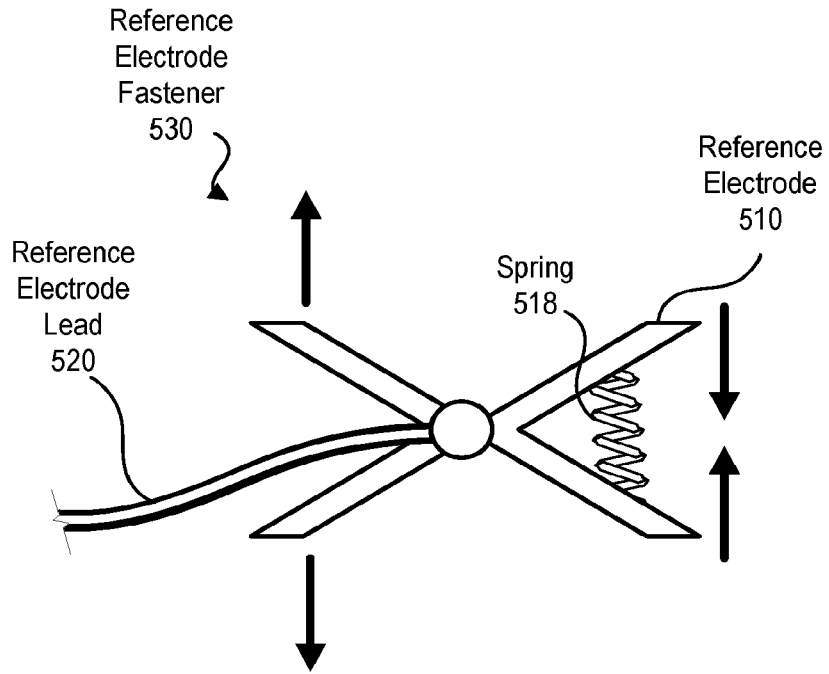
FIG. 37 illustrates an example implementation of a reference electrode having a reference electrode fastener configured as a clip in accordance with certain embodiments herein.

FIG. 37 illustrates an example implementation of a reference electrode 510 having a reference electrode fastener 530 configured as a clip. For example, the reference electrode fastener 530 can be clip the reference electrode 510 to target anatomy. As illustrated, the reference electrode fastener 530 includes a spring 518 that forces together a distal portion of the reference electrode fastener 530 at which the reference electrode 510 is disposed, which forces apart a distal portion of the fastener 530. The reference electrode fastener 530 can have a resting closed state. For instance, absent an outside force, the spring 518 causes the distal portion of the fastener 530 to close together. A clinician can force apart the distal portion by pressing the proximal portion of the fastener 530 together.

FIG. 38 illustrates an example configuration of the reference electrode system 500 in which the reference electrode system 500 can extend an existing reference electrode 560. In the illustrated configuration, the distal portion of the reference electrode lead 520 is electrically coupled to the reference electrode 510 and a proximal portion of the reference electrode lead is coupled to a reference electrode connector 550. The reference electrode connector 550 can be configured to couple with an existing reference electrode 560 to electrically connect the existing reference electrode 560 with the reference electrode 510. In this manner, the reference electrode system 500 can act as an extension to an existing reference electrode 560 to add additional length or fixation capabilities.

FIG. 39 illustrates an example sensory prosthesis that can benefit from use of the technologies disclosed herein: a cochlear implant system 610. The cochlear implant system 610 includes an implantable component 644 typically having an internal receiver/transceiver unit 632, a stimulator unit 620, and an elongate lead 618. The internal receiver/transceiver unit 632 permits the cochlear implant system 610 to receive signals from and/or transmit signals to an external device 650. The external device 650 can be a button sound processor worn on the head that includes a receiver/transceiver coil 630 and sound processing components. Alternatively, the external device 650 can be just a transmitter/transceiver coil in communication with a behind-the-ear device that includes the sound processing components and microphone.

The implantable component 644 includes an internal coil 636, and preferably, a magnet (not shown) fixed relative to the internal coil 636. The magnet can be embedded in a pliable silicone or other biocompatible encapsulant, along with the internal coil 636. Signals sent generally correspond to external sound 613. The internal receiver/transceiver unit 632 and the stimulator unit 620 are hermetically sealed within a biocompatible housing, sometimes collectively referred to as a stimulator/receiver unit. Included magnets (not shown) can facilitate the operational alignment of an external coil 630 and the internal coil 636, enabling the internal coil 636 to receive power and stimulation data from the external coil 630. The external coil 630 is contained within an external portion. The elongate lead 618 has a proximal end connected to the stimulator unit 620, and a distal end 646 implanted in a cochlea 640 of the recipient. The elongate lead 618 extends from stimulator unit 620 to the cochlea 640 through a mastoid bone 619 of the recipient. The elongate lead 618 is used to provide electrical stimulation to the cochlea 640 based on the stimulation data. The stimulation data can be created based on the external sound 613 using the sound processing components and based on the sensory prosthesis settings. As illustrated, the stimulator unit 620 further includes the stimulator 156 configured to deliver stimulation to vestibular tissue of the recipient via electrodes of the body 110 disposed proximate the oval window of the recipient. The lead 140 connects the stimulator 156 to the electrodes of the body 110.

In certain examples, the external coil 630 transmits electrical signals (e.g., power and stimulation data) to the internal coil 636 via a radio frequency (RF) link. The internal coil 636 is typically a wire antenna coil having multiple turns of electrically insulated single-strand or multi-strand platinum or gold wire. The electrical insulation of the internal coil 636 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Other sensory prostheses can benefit from technologies described herein. For example, the technology disclosed herein can be implemented with a direct acoustic stimulator prosthesis configured to generate vibrations and conduct the vibrations to move perilymph in scala tympani to activate hair cells to cause hearing percepts. Such a stimulator can include an actuator, a stapes prosthesis and a coupling element connecting the actuator to the stapes prosthesis. In an example, the prosthesis stimulation arrangement can be implanted and/or configured such that a portion of stapes prosthesis abuts a recipient's round or oval window. In examples, the portion of the prosthesis that abuts the oval window can include one or more electrodes 112 described herein for stimulating vestibular anatomy.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein. Further, the techniques described herein can be applicable to determining a recipient's response to other stimuli, such as visual stimuli, tactile stimuli, olfactory stimuli, taste stimuli, or another stimuli. Likewise, the devices used herein need not be limited to auditory prostheses and can be other medical devices configured to support a human sense, such as bionic eyes.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

The invention claimed is:

1. A method comprising:
   surgically accessing an implantation area in a recipient;
   placing a first surface of a flexible body of a vestibular stimulation prosthesis against an oval window of the recipient, the flexible body having a second surface substantially opposed to the first surface, wherein the first surface includes at least a first electrode and a second electrode, wherein the first electrode and the second electrode are configured to stimulate vestibular tissue of the recipient to provide a sense of balance to the recipient;
   implanting the flexible body at least partially in contact with an ossicular chain of the recipient; and
   implanting, remote from the flexible body, an implantable housing including a stimulator, wherein the stimulator is electrically connected to the first electrode and the second electrode via a lead.

2. The method of claim 1, wherein implanting the flexible body includes placing the flexible body between a stapes of the ossicular chain and the oval window.

3. The method of claim 1, further including:
placing the first surface of the flexible body against the oval window without the at least first electrode or the second electrode penetrating the oval window.

4. The method of claim 1, wherein implanting the flexible body includes:
performing a mastoidectomy;
enlarging a posterior tympanotomy; and
excavating ossicular chain tissue define a location for implanting the flexible body.

5. The method of claim 1, further comprising:
calibrating the vestibular stimulation prosthesis; and
providing therapeutic stimulation with the vestibular stimulation prosthesis.

6. The method of claim 5, wherein calibrating the vestibular stimulation prosthesis includes:
performing vestibular response telemetry.

7. The method of claim 1, further comprising:
placing a material between the flexible body and a facial nerve of the recipient.

8. The method of claim 1, further comprising:
delivering stimulation signals to the vestibular tissue of the recipient by independently using the first electrode and the second electrode.

9. The method of claim 1, wherein the vestibular tissue includes one or more from a group of an otolith organ and a vestibular canal.

10. The method of claim 1, further comprising:
connecting the flexible body to one or more bones of the recipient's ossicular chain.

11. The method of claim 1, further comprising:
removing at least a portion of an incus of the recipient's ossicular chain.

12. The method of claim 1, wherein implanting the flexible body includes transtympanically implanting the flexible body.

13. A method comprising:
surgically accessing an implantation area in a recipient;
implanting a flexible body of a vestibular stimulation prosthesis between an oval window of the recipient and a bone of the auditory ossicles of the recipient; and
implanting, remote from the flexible body, an implantable housing including a stimulator, wherein the stimulator is electrically connected to a first electrode and a second electrode of the flexible body via a lead,
wherein the flexible body comprises a first surface and a second surface substantially opposed to the first surface, the first surface includes at least the first electrode and the second electrode, and the first electrode and the second electrode are configured to stimulate vestibular tissue of the recipient to provide a sense of balance to the recipient.

14. The method of claim 13, further comprising:
performing a mastoidectomy;
enlarging a posterior tympanotomy; and
excavating ossicular chain tissue define a location for implanting the flexible body.

15. The method of claim 13, further comprising:
calibrating the vestibular stimulation prosthesis; and
providing therapeutic stimulation with the vestibular stimulation prosthesis.

16. The method of claim 13, further comprising inserting the first electrode and the second electrode of the flexible body through the oval window to a depth of 2.5 mm or less, 2 mm or less, 1.5 mm or less, 1 mm or less, or 0.5 mm or less.

17. The method of claim 13, further comprising:
removing at least a portion of a stapes of the recipient to make room for the flexible body.

18. A method comprising:
performing a mastoidectomy;
enlarging a posterior tympanotomy;
excavating ossicular chain tissue of a recipient to create an implantation cavity; and
implanting a flexible body of a vestibular stimulation prosthesis in the implantation cavity between an oval window of the recipient and a bone of the auditory ossicles of the recipient, the flexible body including at least a first electrode and a second electrode, wherein the first electrode and the second electrode are configured to stimulate vestibular tissue of the recipient to provide a sense of balance to the recipient; and
implanting, remote from the flexible body, an implantable housing including a stimulator, wherein the stimulator is electrically connected to a first electrode and a second electrode of the flexible body via a lead.

19. The method of claim 18, wherein the first electrode and the second electrode are disposed on a first surface of the flexible body, and the method includes placing the first surface of the flexible body against an oval window of the recipient.

* * * * *